US011214615B2

(12) United States Patent
Wang et al.

(10) Patent No.: US 11,214,615 B2
(45) Date of Patent: Jan. 4, 2022

(54) ANTI-TIM-3 ANTIBODIES AND USES THEREOF

(71) Applicant: Phanes Therapeutics, Inc., San Diego, CA (US)

(72) Inventors: Minghan Wang, San Diego, CA (US); Hui Zou, Dallas, TX (US)

(73) Assignee: Phanes Therapeutics, Inc., San Diego, CA (US)

( * ) Notice: Subject to any disclaimer, the term of this patent is extended or adjusted under 35 U.S.C. 154(b) by 103 days.

(21) Appl. No.: 16/633,262

(22) PCT Filed: Jul. 26, 2018

(86) PCT No.: PCT/US2018/043800
§ 371 (c)(1),
(2) Date: Jan. 23, 2020

(87) PCT Pub. No.: WO2019/023410
PCT Pub. Date: Jan. 31, 2019

(65) Prior Publication Data
US 2021/0032330 A1 Feb. 4, 2021

Related U.S. Application Data

(60) Provisional application No. 62/538,277, filed on Jul. 28, 2017.

(51) Int. Cl.
*C07K 16/28* (2006.01)
*G01N 33/68* (2006.01)
*A61K 39/00* (2006.01)

(52) U.S. Cl.
CPC ... *C07K 16/2803* (2013.01); *A61K 39/001111* (2018.08); *G01N 33/68* (2013.01); *C07K 2317/21* (2013.01); *C07K 2317/24* (2013.01); *C07K 2317/31* (2013.01); *C07K 2317/76* (2013.01); *C07K 2317/92* (2013.01); *G01N 2333/70503* (2013.01)

(58) Field of Classification Search
None
See application file for complete search history.

(56) References Cited

U.S. PATENT DOCUMENTS

| 7,919,086 | B2 | 4/2011 | Nakano et al. | |
|---|---|---|---|---|
| 2012/0189617 | A1* | 7/2012 | Takayanagi | A61P 17/02 424/133.1 |
| 2013/0022623 | A1* | 1/2013 | Karsunky | A61K 33/243 424/173.1 |
| 2014/0302039 | A1 | 10/2014 | Jeong et al. | |
| 2015/0218274 | A1* | 8/2015 | Sabatos-Peyton | A61P 1/04 424/136.1 |
| 2017/0198041 | A1 | 7/2017 | Sabatos-Peyton et al. | |

FOREIGN PATENT DOCUMENTS

| CN | 103173412 A | 6/2013 |
|---|---|---|
| WO | 2003063792 A2 | 8/2003 |
| WO | 2006006693 A1 | 1/2006 |
| WO | 2009052623 A1 | 4/2009 |
| WO | 2010117057 A1 | 10/2010 |
| WO | 2011155607 A1 | 12/2011 |
| WO | 2011159877 A2 | 12/2011 |
| WO | 2013006490 A2 | 1/2013 |
| WO | 2014190273 A1 | 11/2014 |
| WO | 2015117002 A1 | 8/2015 |
| WO | 2016068802 A1 | 5/2016 |
| WO | 2016068803 A1 | 5/2016 |
| WO | 2016071448 A1 | 5/2016 |
| WO | 2016111947 A2 | 7/2016 |
| WO | 2016144803 A2 | 9/2016 |
| WO | 2016161270 A1 | 10/2016 |
| WO | 2017010106 A1 | 1/2017 |
| WO | 2017019897 A1 | 2/2017 |
| WO | 2017031242 A1 | 2/2017 |
| WO | 2017055393 A1 | 4/2017 |
| WO | 2017055404 A1 | 4/2017 |
| WO | 2017079115 A1 | 5/2017 |
| WO | 2017189959 A1 | 11/2017 |

OTHER PUBLICATIONS

Ranferi Ocana-Guzman et al., "TIM-3 Regulates Distinct Functions in Macrophages," Frontiers in Immunology, Jun. 2016, vol. 7, article 229, pp. 1-9.
International Search Report and Written Opinion dated Dec. 7, 2018 in International Application No. PCT/US2018/043800.
BD Pharmingen. Mouse Anti-Human TIM-3 (CD366) Clone 7D3. Technical Data Sheet, 2015 [online]. [Retrieved on Sep. 4, 2018]. Retrieved from the Internet <URL: http://www.bdbiosciences.com/ds/pm/tds/565570.pdf>; in entirety.
UniProtKB/TrEMBL Direct Submission. K7T9R4_MOUSE. May 10, 2017 [online]. [Retrieved on Oct. 1, 2018]. Retrieved from the Internet <URL: https://www.uniprot.org/uniprot/K7T9R4.txt?version=11>; in entirety, especially, amino acids 87-93, 100% identity to Seq ID No. 169, wherein X4 is Ala, X5 is Me.
Kaori Sakuishi et al., "Emerging TIM-3 functions in antimicrobial and tumor immunity," Trends in Immunology, vol. 32, No. 8, pp. 345-349 (2011).

* cited by examiner

Primary Examiner — Nelson B Moseley, II
(74) Attorney, Agent, or Firm — Ice Miller LLP

(57) ABSTRACT

Anti-TIM-3 antibodies and antigen-binding fragments thereof are described. Also described are nucleic acids encoding the antibodies, compositions comprising the antibodies, and methods of producing the antibodies and using the antibodies for treating or preventing diseases such as cancer, an inflammatory disease, an autoimmune disease, a metabolic disease, and/or infectious diseases.

18 Claims, 5 Drawing Sheets

Specification includes a Sequence Listing.

ANTI-TIM-3 ANTIBODIES AND USES THEREOF

CROSS REFERENCE TO RELATED APPLICATIONS

This application is a Section 371 of International Application No. PCT/US2018/043800, filed Jul. 26, 2018, which published in the English language on Jan. 31, 2019 under International Publication No. WO 2019/023410 A1, which claims priority to U.S. Provisional Application No. 62/538,277, filed on Jul. 28, 2017. Each disclosure is incorporated herein by reference in its entirety.

FIELD OF THE INVENTION

This invention relates to monoclonal anti-TIM-3 antibodies, nucleic acids and expression vectors encoding the antibodies, recombinant cells containing the vectors, and compositions comprising the antibodies. Methods of making the antibodies, and methods of using the antibodies to treat diseases including cancer, inflammatory diseases, autoimmune diseases, infectious diseases, metabolic diseases (e.g., obesity, insulin resistance, and diabetes), and/or associated complications are also provided.

REFERENCE TO SEQUENCE LISTING SUBMITTED ELECTRONICALLY

This application contains a sequence listing, which is submitted electronically via EFS-Web as an ASCII formatted sequence listing with a file name "689204.3U1 Sequence Listing" and a creation date of Jan. 15, 2020, and having a size of 78 kb. The sequence listing submitted via EFS-Web is part of the specification and is herein incorporated by reference in its entirety.

BACKGROUND OF THE INVENTION

T-cell immunoglobulin and mucin-domain containing molecule 3 (TIM-3) is a receptor expressed on myeloid cells, including dendritic cells (DCs), macrophages and NK cells, and a subset of lymphoid cells, such as T cells. The documented ligands for TIM-3 include galectin-9 (Gal-9), phosphatidylserine (PtdSer), and high mobility group protein B1 (HMGB1). The ligations of Gal-9 and PtdSer are mediated by the variable immunoglobulin domain (IgV) of TIM-3. The glycosylation of IgV is required for Gal-9 binding but not for PtdSer binding. By interacting with these ligands, TIM-3 modulates both innate and adaptive immunities. HMGB1 also plays an important role in chronic inflammation of the adipose tissue in obesity, suggesting that TIM-3 function could be involved in inflammation-related metabolic changes.

On the surface of myeloid cells, high expression of TIM-3 inhibits the production of cytokines from macrophages and DCs. The inhibition can be reversed by stimulus from T cells and similarly by blocking monoclonal antibodies. In tumors, the cancer protective and promoting M2 macrophages are associated with high level of TIM-3 expression, whereas the cancer fighting M1 macrophages are associated with low level of TIM-3 expression. It remains to be demonstrated whether blocking TIM-3 by a monoclonal antibody can convert M2 to cancer engulfing M1 macrophages.

On the surface of T cells, TIM-3 modulates adaptive immunity by interacting with the ligand Gal-9. TIM-3 is expressed on CD4+ helper (Th1 and Th17), regulatory ($T_{reg}$) and $CD8^+$ cytotoxic 1 (Tc1) T cells. Chronic ligation of TIM-3 to Gal-9 induces apoptosis of Th1 cells, downregulating immune response and duration. The surface expression, or possibly the function, of TIM-3 depends on the binding to CEACAM1 in both cis and trans. Remarkably, TIM-3 is usually found on $CD8^+$ T cells expressing immune-repressing PD-1. It has been proposed that TIM-3 and PD-1 are co-suppressors leading to dysfunctional intratumoral T cells. This makes a TIM-3 antagonist antibody a potentially great therapeutic alone and in combination with a PD-1/PDL-1 and/or other immuno-oncology therapy.

In addition to modulating immune cells, TIM-3 is also highly expressed on the leukemic stem cells (LSCs) in acute myeloid leukemia (AML). On LSCs, TIM-3 and Gal-9 form an autocrine stimulatory loop to drive self-renewal pathways of cancerous LSCs and leukemic progression. Interestingly, TIM-3 is not present on the surface of hematopoietic stem cells (HSCs), providing an opportunity to treat AML and other myeloid leukemia disorders using a blocking/depleting/cytotoxic therapeutic TIM-3 antibody.

TIM-3 modulates the activities of both innate and adaptive immune cells. A TIM-3 blocking monoclonal antibody has the potential to unleash the immune system via unique mechanisms to eliminate cancer cells.

BRIEF SUMMARY OF THE INVENTION

In one general aspect, the invention relates to isolated monoclonal antibodies or antigen-binding fragments thereof that bind TIM-3.

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:

(1) SEQ ID NOs:43, 44, 169, 106, 107, and 170, respectively;
(2) SEQ ID NOs:55, 56, 57, 118, 119, and 120, respectively;
(3) SEQ ID NOs:58, 59, 60, 121, 122, and 123, respectively;
(4) SEQ ID NOs:61, 62, 63, 124, 125, and 126, respectively;
(5) SEQ ID NOs:64, 65, 66, 127, 128, and 129, respectively;
(6) SEQ ID NOs:67, 68, 69, 130, 131, and 132, respectively;
(7) SEQ ID NOs:70, 71, 72, 133, 134, and 135, respectively;
(8) SEQ ID NOs:73, 74, 75, 136, 137, and 138, respectively;
(9) SEQ ID NOs:76, 77, 78, 139, 140, and 141, respectively;
(10) SEQ ID NOs:79, 80, 81, 142, 143, and 144, respectively;
(11) SEQ ID NOs:82, 83, 84, 145, 146, and 147, respectively;
(12) SEQ ID NOs:85, 86, 87, 148, 149, and 150, respectively;
(13) SEQ ID NOs:88, 89, 90, 151, 152, and 153, respectively;
(14) SEQ ID NOs:91, 92, 93, 154, 155, and 156, respectively;
(15) SEQ ID NOs:94, 95, 96, 157, 158, and 159, respectively;

(16) SEQ ID NOs:97, 98, 99, 160, 161, and 162, respectively;

(17) SEQ ID NOs:100, 101, 102, 163, 164, and 165, respectively; or

(18) SEQ ID NOs:103, 104, 105, 166, 167, and 168, respectively;

wherein the antibody or antigen-binding fragment thereof specifically binds TIM-3, preferably human TIM-3. SEQ ID NO:169 is represented by the amino acid sequence ARDX$_1$X$_2$DY, wherein X$_1$ is an amino acid selected from the group consisting of A, T, and L, and wherein X$_2$ is an amino acid selected from M and E. SEQ ID NO:170 is represented by the amino acid sequence SQX$_1$X$_2$HVPX$_3$T, wherein X$_1$ is an amino acid selected from the group consisting of N, T, and S, X$_2$ is an amino acid selected from T and I, and X$_3$ is an amino acid selected from W and Y.

In certain embodiments, the isolated monoclonal antibody or antigen-binding fragment comprise a heavy chain variable region having a polypeptide sequence at least 95% identical to SEQ ID NO:1, 3, 5, 7, 9, 11, 13, 15, 17, 19, 21, 23, 25, 27, 29, 31, 33, 35, 37, 39, or 41 or a light chain variable region having a polypeptide sequence at least 95% identical to SEQ ID NO:2, 4, 6, 8, 10, 12, 14, 16, 18, 20, 22, 24, 26, 28, 30, 32, 34, 36, 38, 40, or 42.

In certain embodiments, the isolated monoclonal antibody or antigen-binding fragment comprise:

(a) a heavy chain variable region having the polypeptide sequence of SEQ ID NO:1, and a light chain variable region having the polypeptide sequence of SEQ ID NO:2;

(b) a heavy chain variable region having the polypeptide sequence of SEQ ID NO:3, and a light chain variable region having the polypeptide sequence of SEQ ID NO:4;

(c) a heavy chain variable region having the polypeptide sequence of SEQ ID NO:5, and a light chain variable region having the polypeptide sequence of SEQ ID NO:6;

(d) a heavy chain variable region having the polypeptide sequence of SEQ ID NO:7, and a light chain variable region having the polypeptide sequence of SEQ ID NO:8;

(e) a heavy chain variable region having the polypeptide sequence of SEQ ID NO:9, and a light chain variable region having the polypeptide sequence of SEQ ID NO:10;

(f) a heavy chain variable region having the polypeptide sequence of SEQ ID NO:11, and a light chain variable region having the polypeptide sequence of SEQ ID NO:12;

(g) a heavy chain variable region having the polypeptide sequence of SEQ ID NO:13, and a light chain variable region having the polypeptide sequence of SEQ ID NO:14;

(h) a heavy chain variable region having the polypeptide sequence of SEQ ID NO:15, and a light chain variable region having the polypeptide sequence of SEQ ID NO:16;

(i) a heavy chain variable region having the polypeptide sequence of SEQ ID NO:17, and a light chain variable region having the polypeptide sequence of SEQ ID NO:18;

(j) a heavy chain variable region having the polypeptide sequence of SEQ ID NO:19, and a light chain variable region having the polypeptide sequence of SEQ ID NO:20;

(k) a heavy chain variable region having the polypeptide sequence of SEQ ID NO:21, and a light chain variable region having the polypeptide sequence of SEQ ID NO:22;

(l) a heavy chain variable region having the polypeptide sequence of SEQ ID NO:23, and a light chain variable region having the polypeptide sequence of SEQ ID NO:24;

(m) a heavy chain variable region having the polypeptide sequence of SEQ ID NO:25, and a light chain variable region having the polypeptide sequence of SEQ ID NO:26;

(n) a heavy chain variable region having the polypeptide sequence of SEQ ID NO:27, and a light chain variable region having the polypeptide sequence of SEQ ID NO:28;

(o) a heavy chain variable region having the polypeptide sequence of SEQ ID NO:29, and a light chain variable region having the polypeptide sequence of SEQ ID NO:30;

(p) a heavy chain variable region having the polypeptide sequence of SEQ ID NO:31, and a light chain variable region having the polypeptide sequence of SEQ ID NO:32;

(q) a heavy chain variable region having the polypeptide sequence of SEQ ID NO:33, and a light chain variable region having the polypeptide sequence of SEQ ID NO:34;

(r) a heavy chain variable region having the polypeptide sequence of SEQ ID NO:35, and a light chain variable region having the polypeptide sequence of SEQ ID NO:36;

(s) a heavy chain variable region having the polypeptide sequence of SEQ ID NO:37, and a light chain variable region having the polypeptide sequence of SEQ ID NO:38;

(t) a heavy chain variable region having the polypeptide sequence of SEQ ID NO:39, and a light chain variable region having the polypeptide sequence of SEQ ID NO:40; or (u) a heavy chain variable region having the polypeptide sequence of SEQ ID NO:41, and a light chain variable region having the polypeptide sequence of SEQ ID NO:42.

In certain embodiments, the isolated monoclonal antibody or antigen-binding fragment thereof is chimeric.

In certain embodiments, the isolated monoclonal antibody or antigen-binding fragment thereof is human or humanized.

In certain embodiments, the humanized monoclonal antibody or antigen-binding fragment thereof comprises:

(a) a heavy chain variable region having the polypeptide sequence of SEQ ID NO:171, and a light chain variable region having the polypeptide sequence of SEQ ID NO:175;

(b) a heavy chain variable region having the polypeptide sequence of SEQ ID NO:172, and a light chain variable region having the polypeptide sequence of SEQ ID NO:175;

(c) a heavy chain variable region having the polypeptide sequence of SEQ ID NO:173, and a light chain variable region having the polypeptide sequence of SEQ ID NO:176; or (d) a heavy chain variable region having the polypeptide sequence of SEQ ID NO:174, and a light chain variable region having the polypeptide sequence of SEQ ID NO:176.

In certain embodiments, the isolated monoclonal antibody or antigen-binding fragment thereof is capable of blocking binding of TIM-3 to phosphatidylserine (PtdSer), TIM-3 to galectin-9 (Gal-9), TIM-3 to carcinoembryonic antigen cell adhesion molecule 1 (CEACAM1), and/or TIM-3 to high mobility group protein B1 (HMGB1).

Also provided are isolated nucleic acids encoding the monoclonal antibodies or antigen-binding fragments thereof of the invention disclosed herein.

Also provided are vectors comprising the isolated nucleic acids encoding the monoclonal antibodies or antigen-binding fragments thereof of the invention.

Also provided are host cells comprising the vectors comprising the isolated nucleic acids encoding the monoclonal antibodies or antigen-binding fragments thereof of the invention.

In certain embodiments, provided is a pharmaceutical composition comprising an isolated monoclonal antibody or antigen-binding fragment thereof of the invention and a pharmaceutically acceptable carrier.

Also provided are methods of blocking binding of TIM-3 to phosphatidylserine (PtdSer), TIM-3 to galectin-9 (Gal-9), TIM-3 to carcinoembryonic antigen cell adhesion molecule 1 (CEACAM1), and/or TIM-3 to high mobility group protein B1 (HMGB1) in a subject in need thereof, comprising administering to the subject the pharmaceutical compositions of the invention.

Also provided are methods of treating cancer in a subject in need thereof, comprising administering to the subject the pharmaceutical compositions of the invention. The cancer can be any liquid or solid cancer, for example, it can be selected from, but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

Also provided are methods of treating an infectious disease in a subject in need thereof, comprising administering to the subject the pharmaceutical composition of the invention.

Also provided are methods of treating an inflammatory disease in a subject in need thereof, comprising administering to the subject the pharmaceutical compositions of the invention.

Also provided are methods of treating an autoimmune disease in a subject in need thereof, comprising administering to the subject the pharmaceutical compositions of the invention.

Also provided are methods of treating a metabolic disease in a subject in need thereof, comprising administering to the subject the pharmaceutical compositions of the invention.

Also provided are methods of producing the monoclonal antibody or antigen-binding fragment thereof of the invention, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or culture.

Also provided are methods of producing a pharmaceutical composition comprising the monoclonal antibody or antigen-binding fragment thereof of the invention, comprising combining the monoclonal antibody or antigen-binding fragment with a pharmaceutically acceptable carrier to obtain the pharmaceutical composition.

Also provided are methods of determining a level of TIM-3 in a subject. The methods comprise (a) obtaining a sample from the subject; (b) contacting the sample with an antibody or antigen-binding fragment thereof of the invention; and (c) determining the level of TIM-3 in the subject. In certain embodiments, the sample is a tissue or blood sample. The tissue sample can, for example, be a cancer tissue sample. The blood sample can, for example, comprise cancer cells.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 1 shows the inhibition of human TIM-3 binding to PtdSer by anti-TIM-3 monoclonal antibodies (mAbs). ELISA plates were coated with PtdSer or PtdChol, washed and incubated with a pre-equilibrated mixture of purified antibodies at various concentrations and TIM3(ECD)-huFc. The plates were washed and then the signal was detected by incubation with HRP-coupled anti-huFc secondary antibody and then a HRP substrate. TIM-3 binding to PtdSer was used as 100% signal and TIM-3 binding to PtdChol as zero (background) to calculate percent of inhibition by a given mAb.

DETAILED DESCRIPTION OF THE INVENTION

Figure 1A:
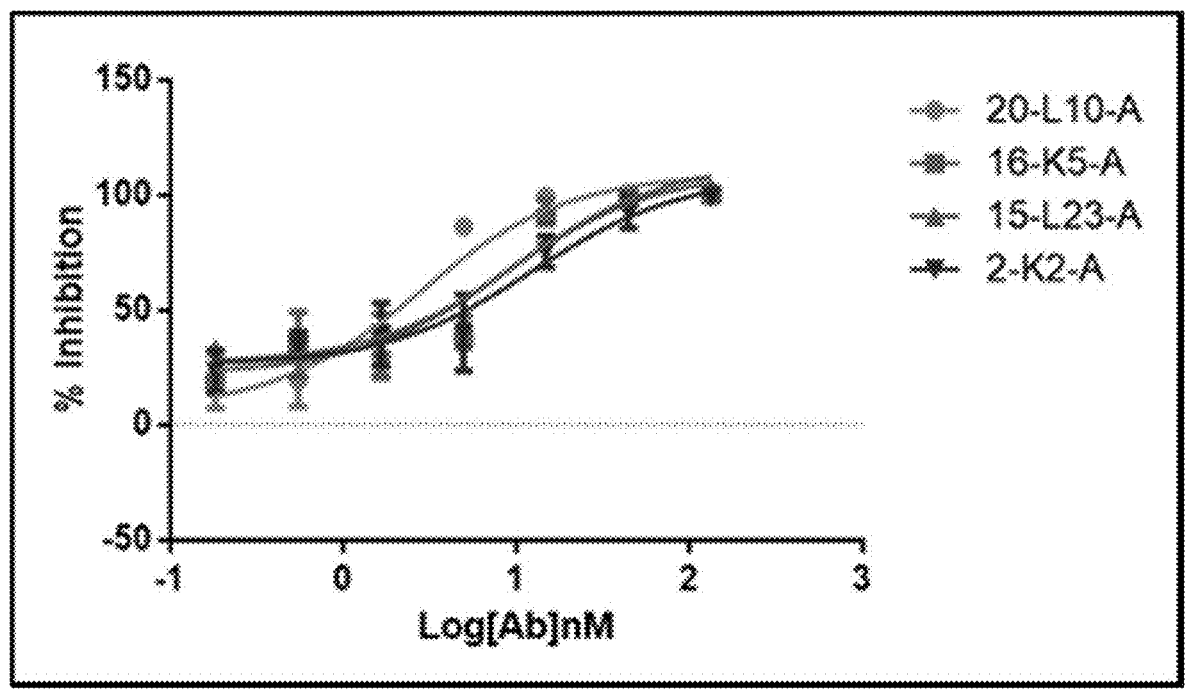
FIG. 1A shows a graph of the inhibition of human TIM-3 binding to PtdSer by anti-TIM-3 antibodies 20-L10-A, 16-K5-A, 15-L23-A, and 2-K2-A.
Figure 1B:
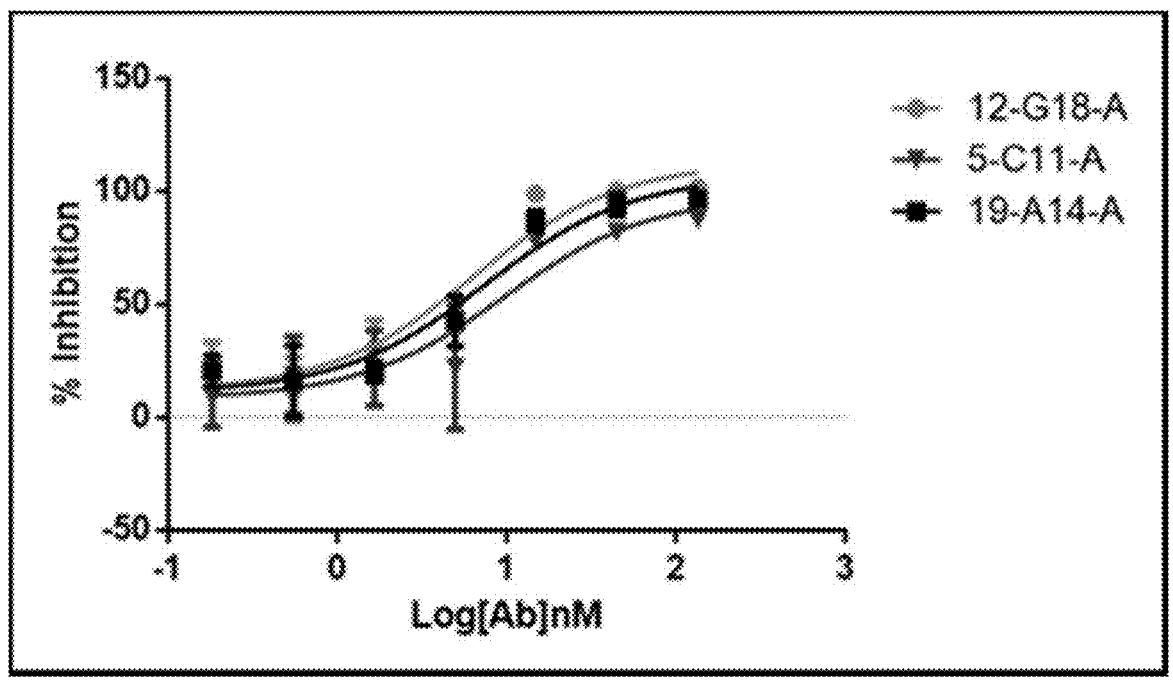
FIG. 1B shows a graph of the inhibition of human TIM-3 binding to PtdSer by anti-TIM-3 antibodies 12-G18-A, 5-C11-A, and 19-A14-A.
Figure 1C:
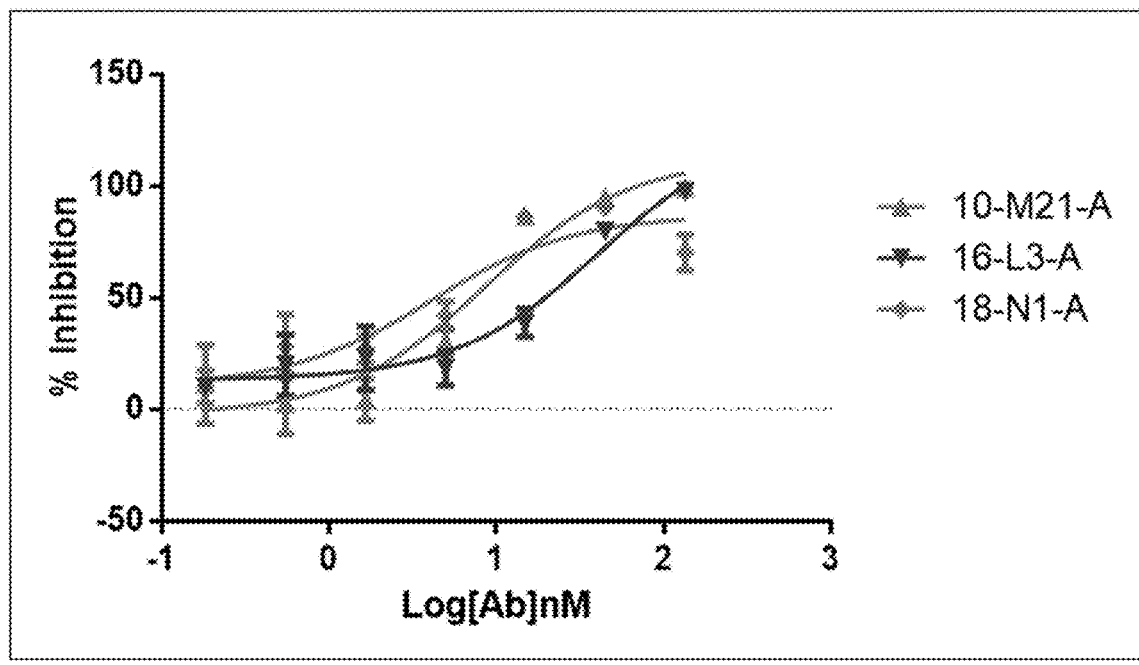
FIG. 1C shows a graph of the inhibition of human TIM-3 binding to PtdSer by anti-TIM-3 antibodies 10-M21-A, 18-N1-A, and 16-L3-A.
Figure 1D:
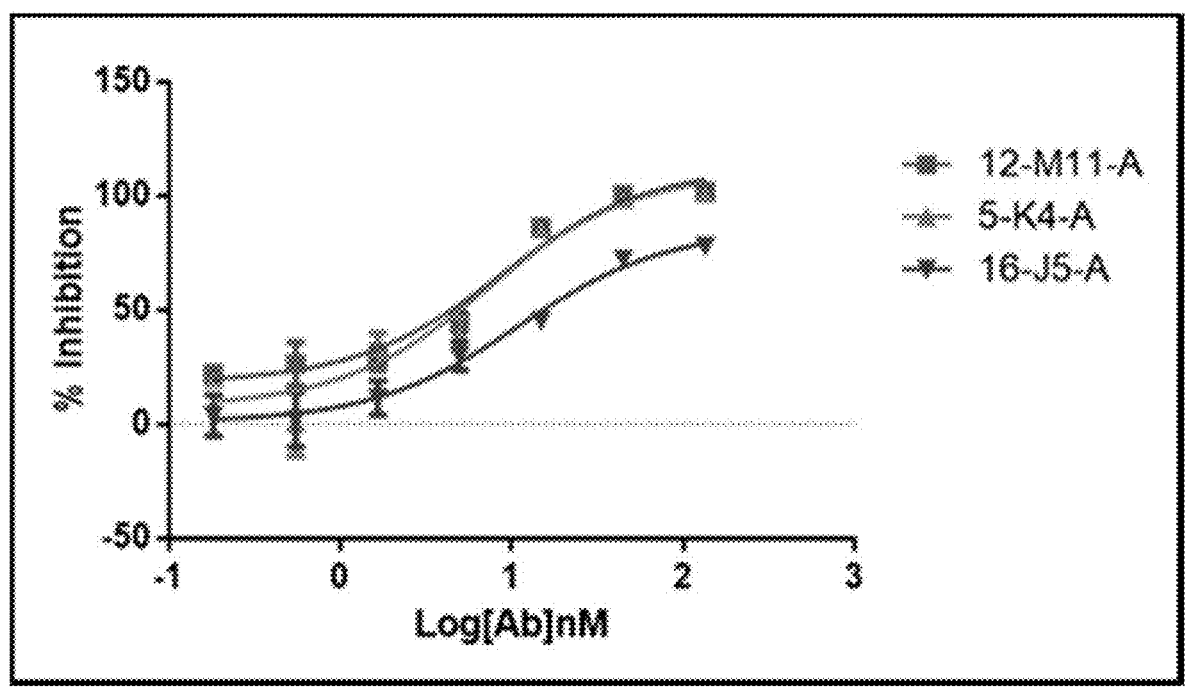
FIG. 1D shows a graph of the inhibition of human TIM-3 binding to PtdSer by anti-TIM-3 antibodies 12-M11-A, 5-K4-A, and 16-J5-A.
Figure 1E:
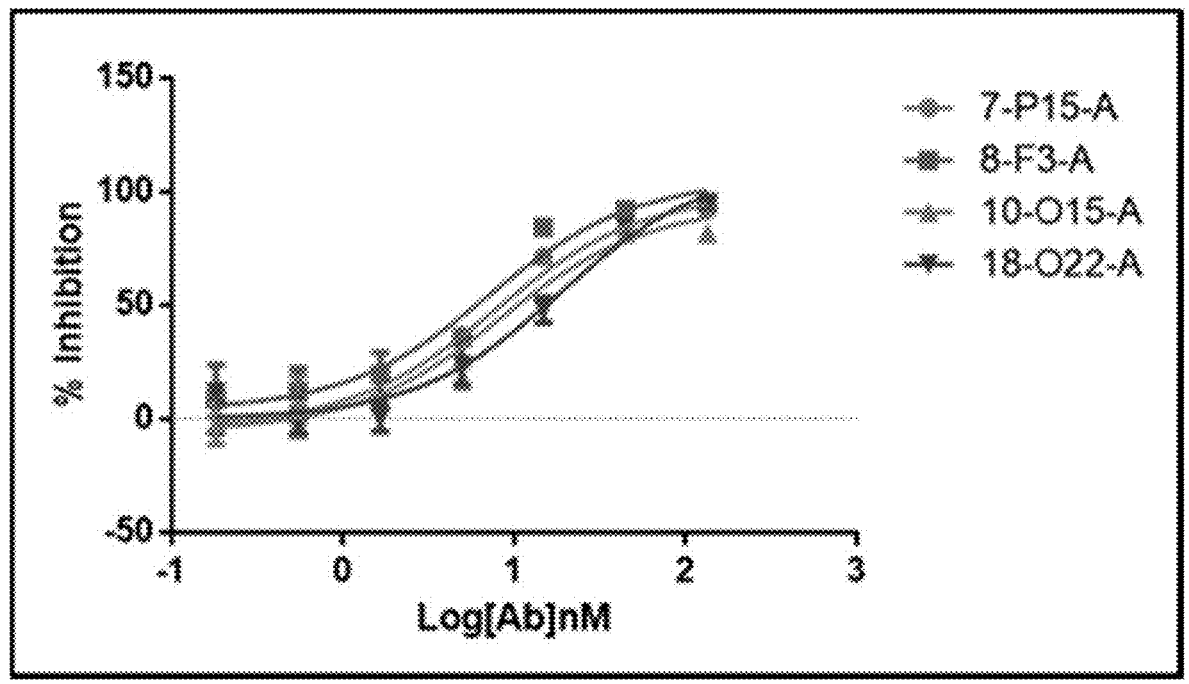
FIG. 1E shows a graph of the inhibition of human TIM-3 binding to PtdSer by anti-TIM-3 antibodies 7-P15-A, 8-F3-A, 10-O15-A, and 18-O22-A.
Figure 1F:
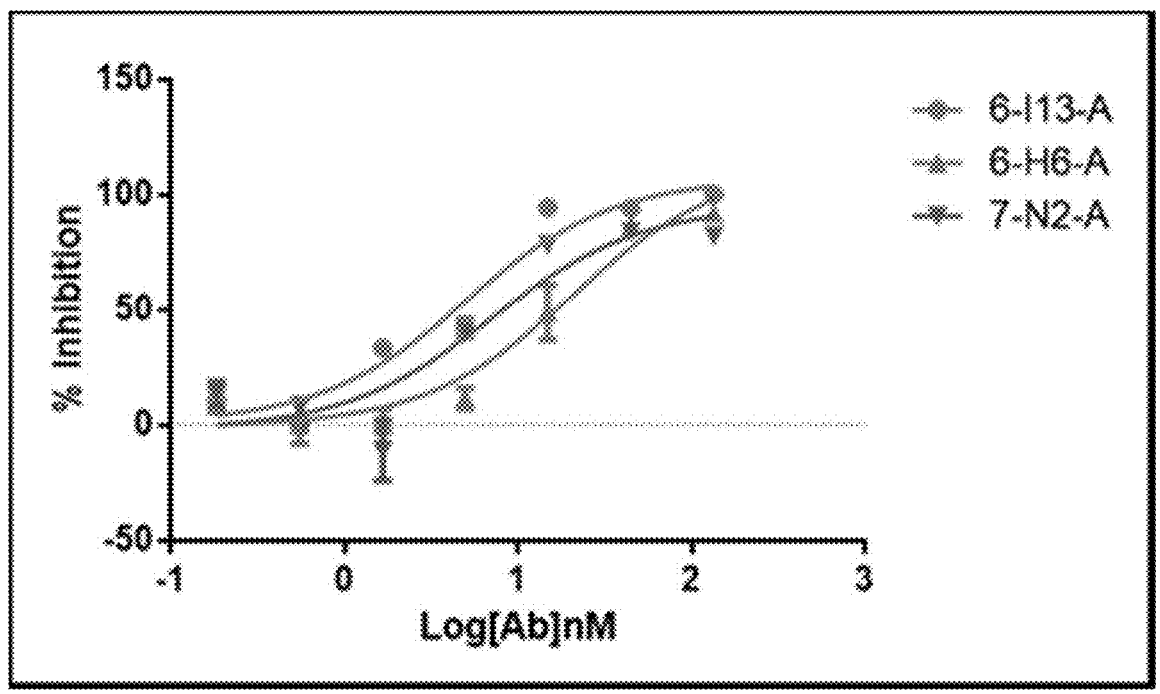
FIG. 1F shows a graph of the inhibition of human TIM-3 binding to PtdSer by anti-TIM-3 antibodies 6-I13-A, 6-H6-A, and 7-N2-A.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right," "left," "lower," and "upper" designate directions in the drawings to which reference is made.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-TIM-3 antibodies, TIM-3 polypeptides, and polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

Antibodies

The invention generally relates to isolated anti-TIM-3 antibodies, nucleic acids and expression vectors encoding the antibodies, recombinant cells containing the vectors, and compositions comprising the antibodies. Methods of making the antibodies, and methods of using the antibodies to treat diseases including cancer, inflammatory diseases, autoimmune diseases, metabolic diseases, and/or infectious diseases are also provided. The antibodies of the invention possess one or more desirable functional properties, including but not limited to high-affinity binding to TIM-3, high specificity to TIM-3, the ability to block the binding of TIM-3 to phosphatidylserine (PtdSer), the ability to block the binding of TIM-3 to galectin-9, the ability to block the binding of TIM-3 to carcinoembryonic antigen cell adhesion molecule 1 (CEACAM1), the ability to block the binding of TIM-3 to high mobility group protein B1 (HMGB1), the ability to stimulate the production of cytokines such as, but not limited to, IL-2 and IFN-γ, and the ability to inhibit tumor growth in animal models and subjects when administered alone or in combination with other anti-cancer therapies.

In a general aspect, the invention relates to isolated monoclonal antibodies or antigen-binding fragments thereof that bind TIM-3.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCRD3, and the heavy chain variable region domains are alternatively referred to as HCDR1, HCRD2, and HCDR3.

As used herein, the term an "isolated antibody" refers to an antibody which is substantially free of other antibodies having different antigenic specificities (e.g., an isolated antibody that specifically binds to TIM-3 is substantially free of antibodies that do not bind to TIM-3). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multi-specific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab'). As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g. the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody, or a tetraspecific antibody molecule.

As used herein, the term "bispecifc antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment the first and second epitopes are on different antigens, e.g., the different proteins (or different subunits of a multimeric protein). In an embodiment a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on TIM-3 and the second epitope is located on PD-1, PD-L1, LAG-3, CTLA-4, EGFR, HER-2, CD19, CD20, CD33, DLL-3, CD73, apelin, CD3, CD47, TIP-1, CLDN18.2, FOLR1 and/or other tumor associated immune suppressors or surface antigens.

As used herein, the term "TIM-3" refers to the T-cell immunoglobulin and mucin-domain containing molecule 3 protein, a receptor expressed on myeloid cells, including dendritic cells (DCs), macrophages and natural killer (NK) cells, and a subset of lymphoid cells, such as T cells. TIM-3 is capable of binding to phosphatidylserine (PtdSer), which is the principal signal for the phagocytosis of apoptotic bodies or cells. When the binding of PtdSer and TIM-3 is blocked with specific antibodies, apoptotic bodies are not removed, which can induce immunological abnormalities, such as the generation of autoantibodies (reviewed in Ocana-Guzman et al., "TIM-3 regulates distinct functions in macrophages," Frontiers in Immunology Vol. 7, Art. 229 (2016)). TIM-3 can regulate the production and release of cytokines in monocytes and macrophages (reviewed in Ocana-Guzman et al., Id). The term "human TIM-3" refers to a TIM-3 originated from a human. An exemplary amino acid sequence of a human TIM-3 is represented in GenBank Accession No. Q8TDQ0.3 or GenBank Accession No. NP_116171.3 (SEQ ID NO:177).

As used herein, an antibody that "specifically binds to TIM-3" refers to an antibody that binds to a TIM-3, preferably a human TIM-3, with a KD of $1\times10^{-7}$ M or less, preferably $1\times10^{-8}$ M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

The smaller the value of the KD of an antibody, the higher affinity that the antibody binds to a target antigen.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:

(1) SEQ ID NOs:43, 44, 169, 106, 107, and 170, respectively;
(2) SEQ ID NOs:55, 56, 57, 118, 119, and 120, respectively;
(3) SEQ ID NOs:58, 59, 60, 121, 122, and 123, respectively;
(4) SEQ ID NOs:61, 62, 63, 124, 125, and 126, respectively;
(5) SEQ ID NOs:64, 65, 66, 127, 128, and 129, respectively;
(6) SEQ ID NOs:67, 68, 69, 130, 131, and 132, respectively;
(7) SEQ ID NOs:70, 71, 72, 133, 134, and 135, respectively;
(8) SEQ ID NOs:73, 74, 75, 136, 137, and 138, respectively;
(9) SEQ ID NOs:76, 77, 78, 139, 140, and 141, respectively;
(10) SEQ ID NOs:79, 80, 81, 142, 143, and 144, respectively;
(11) SEQ ID NOs:82, 83, 84, 145, 146, and 147, respectively;
(12) SEQ ID NOs:85, 86, 87, 148, 149, and 150, respectively;
(13) SEQ ID NOs:88, 89, 90, 151, 152, and 153, respectively;
(14) SEQ ID NOs:91, 92, 93, 154, 155, and 156, respectively;
(15) SEQ ID NOs:94, 95, 96, 157, 158, and 159, respectively;
(16) SEQ ID NOs:97, 98, 99, 160, 161, and 162, respectively;
(17) SEQ ID NOs:100, 101, 102, 163, 164, and 165, respectively; or
(18) SEQ ID NOs:103, 104, 105, 166, 167, and 168, respectively;
wherein the antibody or antigen-binding fragment thereof specifically binds TIM-3, preferably human TIM-3.

SEQ ID NO:169 is represented by the amino acid sequence ARDX$_1$X$_2$DY, wherein X$_1$ is an amino acid selected from the group consisting of A, T, and L, and wherein X$_2$ is an amino acid selected from M and E.

SEQ ID NO:170 is represented by the amino acid sequence SQX$_1$X$_2$HVPX$_3$T, wherein X$_1$ is an amino acid selected from the group consisting of N, T, and S, X$_2$ is an amino acid selected from T and I, and X$_3$ is an amino acid selected from W and Y.

According to another particular aspect, the invention relates to an isolated monoclonal antibody or antigen-binding fragment thereof comprising a heavy chain variable region having a polypeptide sequence at least 85%, preferably 90%, more preferably 95% identical to one of SEQ ID NOs:1, 3, 5, 7, 9, 11, 13, 15, 17, 19, 21, 23, 25, 27, 29, 31, 33, 35, 37, 39, or 41, or a light chain variable region having a polypeptide sequence at least 85%, preferably 90%, more preferably 95% identical to one of SEQ ID NOs:2, 4, 6, 8, 10, 12, 14, 16, 18, 20, 22, 24, 26, 28, 30, 32, 34, 36, 38, 40, or 42. According to one preferred embodiment, the isolated monoclonal antibody or antigen-binding fragment thereof of the invention comprises a heavy chain variable region having the polypeptide sequence at least 85%, preferably 90%, more preferably 95% identical to SEQ ID NO:1, 3, 5, 7, 9, 11, 13, 15, 17, 19, 21, 23, 25, 27, 29, 31, 33, 35, 37, 39, or 41, and a light chain variable region having a polypeptide sequence at least 85%, preferably 90%, more preferably 95% identical to SEQ ID NO:2, 4, 6, 8, 10, 12, 14, 16, 18, 20, 22, 24, 26, 28, 30, 32, 34, 36, 38, 40, or 42, respectively.

According to another particular aspect, the invention relates to an isolated monoclonal antibody or antigen-binding fragment thereof of the invention, comprising:
a. a heavy chain variable region having the polypeptide sequence of SEQ ID NO:1, and a light chain variable region having the polypeptide sequence of SEQ ID NO:2;
b. a heavy chain variable region having the polypeptide sequence of SEQ ID NO:3, and a light chain variable region having the polypeptide sequence of SEQ ID NO:4;
c. a heavy chain variable region having the polypeptide sequence of SEQ ID NO:5, and a light chain variable region having the polypeptide sequence of SEQ ID NO:6;
d. a heavy chain variable region having the polypeptide sequence of SEQ ID NO:7, and a light chain variable region having the polypeptide sequence of SEQ ID NO:8;
e. a heavy chain variable region having the polypeptide sequence of SEQ ID NO:9, and a light chain variable region having the polypeptide sequence of SEQ ID NO:10;
f. a heavy chain variable region having the polypeptide sequence of SEQ ID NO:11, and a light chain variable region having the polypeptide sequence of SEQ ID NO:12;
g. a heavy chain variable region having the polypeptide sequence of SEQ ID NO:13, and a light chain variable region having the polypeptide sequence of SEQ ID NO:14;
h. a heavy chain variable region having the polypeptide sequence of SEQ ID NO:15, and a light chain variable region having the polypeptide sequence of SEQ ID NO:16;
i. a heavy chain variable region having the polypeptide sequence of SEQ ID NO:17, and a light chain variable region having the polypeptide sequence of SEQ ID NO:18;
j. a heavy chain variable region having the polypeptide sequence of SEQ ID NO:19, and a light chain variable region having the polypeptide sequence of SEQ ID NO:20;
k. a heavy chain variable region having the polypeptide sequence of SEQ ID NO:21, and a light chain variable region having the polypeptide sequence of SEQ ID NO:22;
l. a heavy chain variable region having the polypeptide sequence of SEQ ID NO:23, and a light chain variable region having the polypeptide sequence of SEQ ID NO:24;
m. a heavy chain variable region having the polypeptide sequence of SEQ ID NO:25, and a light chain variable region having the polypeptide sequence of SEQ ID NO:26;
n. a heavy chain variable region having the polypeptide sequence of SEQ ID NO:27, and a light chain variable region having the polypeptide sequence of SEQ ID NO:28;

o. a heavy chain variable region having the polypeptide sequence of SEQ ID NO:29, and a light chain variable region having the polypeptide sequence of SEQ ID NO:30;
p. a heavy chain variable region having the polypeptide sequence of SEQ ID NO:31, and a light chain variable region having the polypeptide sequence of SEQ ID NO:32;
q. a heavy chain variable region having the polypeptide sequence of SEQ ID NO:33, and a light chain variable region having the polypeptide sequence of SEQ ID NO:34;
r. a heavy chain variable region having the polypeptide sequence of SEQ ID NO:35, and a light chain variable region having the polypeptide sequence of SEQ ID NO:36;
s. a heavy chain variable region having the polypeptide sequence of SEQ ID NO:37, and a light chain variable region having the polypeptide sequence of SEQ ID NO:38;
t. a heavy chain variable region having the polypeptide sequence of SEQ ID NO:39, and a light chain variable region having the polypeptide sequence of SEQ ID NO:40; or
u. a heavy chain variable region having the polypeptide sequence of SEQ ID NO:41, and a light chain variable region having the polypeptide sequence of SEQ ID NO:42.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:43, 44, 45, 106, 107, and 108, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:1, and a light chain variable region having a polypeptide sequence at least 85%, preferably 90%, more preferably 95% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:46, 47, 48, 109, 110, and 111, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:3, and a light chain variable region having a polypeptide sequence at least 85%, preferably 90%, more preferably 95% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:49, 50, 51, 112, 113, and 114, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:5, and a light chain variable region having a polypeptide sequence at least 85%, preferably 90%, more preferably 95% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:52, 53, 54, 115, 116, and 117, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:7, and a light chain variable region having a polypeptide sequence at least 85%, preferably 90%, more preferably 95% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:55, 56, 57, 118, 119, and 120, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:9, and a light chain variable region having a polypeptide sequence at least 85%, preferably 90%, more preferably 95% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:58, 59, 60, 121, 122, and 123, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:11, and a light chain variable region having a polypeptide sequence at least 85%, preferably 90%, more preferably 95% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:61, 62, 63, 124, 125, and 126, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:13, and a light chain variable region having a polypeptide sequence at least 85%, preferably 90%, more preferably 95% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:64, 65, 66, 127, 128, and 129, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:15, and a light chain variable region having a polypeptide sequence at least 85%, preferably 90%, more preferably 95% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:67, 68, 69, 130, 131, and 132, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:17, and a light chain variable region having a polypeptide sequence at least 85%, preferably 90%, more preferably 95% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:70, 71, 72, 133, 134, and 135, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:19, and a light chain variable region having a polypeptide sequence at least 85%, preferably 90%, more preferably 95% identical to SEQ ID NO:20. Preferably, the isolated monoclonal antibody or antigen-binding fragment thereof comprises a heavy chain variable region having the polypeptide sequence of SEQ ID NO:19; and a light chain variable region having the polypeptide sequence of SEQ ID NO:20.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:73, 74, 75, 136, 137, and 138, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:21, and a light chain variable region having a polypeptide sequence at least 85%, preferably 90%, more preferably 95% identical to SEQ ID NO:22. Preferably, the isolated monoclonal antibody or antigen-binding fragment thereof comprises a heavy chain variable region having the polypeptide sequence of SEQ ID NO:21; and a light chain variable region having the polypeptide sequence of SEQ ID NO:22.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:76, 77, 78, 139, 140, and 141, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:23, and a light chain variable region having a polypeptide sequence at least 85%, preferably 90%, more preferably 95% identical to SEQ ID NO:24. Preferably, the isolated monoclonal antibody or antigen-binding fragment thereof comprises a heavy chain variable region having the polypeptide sequence of SEQ ID NO:23; and a light chain variable region having the polypeptide sequence of SEQ ID NO:24.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:79, 80, 81, 142, 143, and 144, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:25, and a light chain variable region having a polypeptide sequence at least 85%, preferably 90%, more preferably 95% identical to SEQ ID NO:26. Preferably, the isolated monoclonal antibody or antigen-binding fragment thereof comprises a heavy chain variable region having the polypeptide sequence of SEQ ID NO:25; and a light chain variable region having the polypeptide sequence of SEQ ID NO:26.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:82, 83, 84, 145, 146, and 147, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:27, and a light chain variable region having a polypeptide sequence at least 85%, preferably 90%, more preferably 95% identical to SEQ ID NO:28. Preferably, the isolated monoclonal antibody or antigen-binding fragment thereof comprises a heavy chain variable region having the polypeptide sequence of SEQ ID NO:27; and a light chain variable region having the polypeptide sequence of SEQ ID NO:28.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:85, 86, 87, 148, 149, and 150, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:29, and a light chain variable region having a polypeptide sequence at least 85%, preferably 90%, more preferably 95% identical to SEQ ID NO:30. Preferably, the isolated monoclonal antibody or antigen-binding fragment thereof comprises a heavy chain variable region having the polypeptide sequence of SEQ ID NO:29; and a light chain variable region having the polypeptide sequence of SEQ ID NO:30.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:88, 89, 90, 151, 152, and 153, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:31, and a light chain variable region having a polypeptide sequence at least 85%, preferably 90%, more preferably 95% identical to SEQ ID NO:32. Preferably, the isolated monoclonal antibody or antigen-binding fragment thereof comprises a heavy chain variable region having the polypeptide sequence of SEQ ID NO:31; and a light chain variable region having the polypeptide sequence of SEQ ID NO:32.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:91, 92, 93, 154, 155, and 156, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:33, and a light chain variable region having a polypeptide sequence at least 85%, preferably 90%, more preferably 95% identical to SEQ ID NO:34. Preferably, the isolated monoclonal antibody or antigen-binding fragment thereof comprises a heavy chain variable region having the polypeptide sequence of SEQ ID NO:33; and a light chain variable region having the polypeptide sequence of SEQ ID NO:34.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:94, 95, 96, 157, 158, and 159, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:35, and a light chain variable region having a polypeptide sequence at least 85%, preferably 90%, more preferably 95% identical to SEQ ID NO:36. Preferably, the isolated monoclonal antibody or antigen-binding fragment thereof comprises a heavy chain variable region having the polypeptide sequence of SEQ ID NO:35; and a light chain variable region having the polypeptide sequence of SEQ ID NO:36.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:97, 98, 99, 160, 161, and 162, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:37, and a light chain variable region having a polypeptide sequence at least 85%, preferably 90%, more preferably 95% identical to SEQ ID NO:38. Preferably, the isolated monoclonal antibody or antigen-binding fragment thereof comprises a heavy chain variable region having the polypeptide sequence of SEQ ID NO:37; and a light chain variable region having the polypeptide sequence of SEQ ID NO:38.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:100, 101, 102, 163, 164, and 165, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:39, and a light chain variable region having a polypeptide sequence at least 85%, preferably 90%, more preferably 95% identical to SEQ ID NO:40. Preferably, the isolated monoclonal antibody or antigen-binding fragment thereof comprises a heavy chain variable region having the polypeptide sequence of SEQ ID NO:39; and a light chain variable region having the polypeptide sequence of SEQ ID NO:40.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:103, 104, 105, 166, 167, and 168, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:41, and a light chain variable region having a polypeptide sequence at least 85%, preferably 90%, more preferably 95% identical to SEQ ID NO:42. Preferably, the isolated monoclonal antibody or antigen-binding fragment thereof comprises a heavy chain variable region having the polypeptide sequence of SEQ ID NO:41; and a light chain variable region having the polypeptide sequence of SEQ ID NO:42.

According to another particular aspect, the invention relates to an isolated monoclonal antibody or antigen-binding fragment thereof of the invention, wherein the antibody or antigen-binding fragment thereof is chimeric.

According to another particular aspect, the invention relates to an isolated monoclonal antibody or antigen-binding fragment thereof of the invention, wherein the antibody or antigen-binding fragment thereof is human or humanized.

According to another particular aspect, the invention relates to an isolated humanized monoclonal antibody or antigen-binding fragment thereof of the invention, wherein the isolated humanized antibody or antigen-binding fragment thereof comprises:
  (a) a heavy chain variable region having the polypeptide sequence of SEQ ID NO:171, and a light chain variable region having the polypeptide sequence of SEQ ID NO:175;
  (b) a heavy chain variable region having the polypeptide sequence of SEQ ID NO:172, and a light chain variable region having the polypeptide sequence of SEQ ID NO:175;

(c) a heavy chain variable region having the polypeptide sequence of SEQ ID NO:173, and a light chain variable region having the polypeptide sequence of SEQ ID NO:176; or (d) a heavy chain variable region having the polypeptide sequence of SEQ ID NO:174, and a light chain variable region having the polypeptide sequence of SEQ ID NO:176.

According to another particular aspect, the invention relates to an isolated monoclonal antibody or antigen-binding fragment thereof of the invention, wherein the antibody or antigen-binding fragment thereof is capable of blocking binding of TIM-3 to phosphatidylserine (PtdSer), TIM-3 to galectin-9 (Gal-9), TIM-3 to carcinoembryonic antigen cell adhesion molecule 1 (CEACAM1), and/or TIM-3 to high mobility group protein B1 (HMGB1).

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated monoclonal antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carriers can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars can be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

Methods of Use

In another general aspect, the invention relates to a method of blocking the binding of TIM-3 to phosphatidylserine (PtdSer), a method of blocking the binding of TIM-3 to galectin-9, a method of blocking the binding of TIM-3 to carcinoembryonic antigen cell adhesion molecule 1 (CEACAM1), or a method of blocking the binding of TIM-3 to high mobility group protein B1 (HMGB1), the method comprising administering to the subject a pharmaceutical composition of the invention.

The functional activity of antibodies and antigen-binding fragments thereof that bind TIM-3 can be characterized by methods known in the art and as described herein. Methods for characterizing antibodies and antigen-binding fragments thereof that bind TIM-3 include, but are not limited to, affinity and specificity assays including Biacore, ELISA, and OctetRed analysis; receptor ligand binding assays to detect blocking of the binding of TIM-3 to PtdSer, galectin-9, CEACAM1, and/or HMGB1; the functional effect of inhibition of PtdSer-TIM-3 interaction by an anti-TIM-3 mAb can be detected in a cell-based phagocytosis assay where TIM-3 expressing macrophages are incubated with cells undergoing apoptosis (and thereby expressing PtdSer) and the mAb's blocking of the PtdSer-TIM-3 interaction leads to increased phagocytosis. The functional effect of inhibition of Gal-9-TIM-3 interaction by an anti-TIM-3 mAb can be detected in a cell-based assay where IFN-γ secretion and cell killing are induced as a result of the mAb's blocking of the binding of Gal-9 on AML cells to TIM-3 on NK cells. The functional effect of inhibition of HMGB1-TIM-3 interaction by an anti-TIM-3 mAb can be detected in a cell-based assay where TIM-3 expressing cells are incubated with B-DNA and the mAb's blocking of the HMGB1-TIM-3 interaction leads to increased INF-β1 production. The functional activity of an anti-TIM-3 mAb can also be assessed in a Mixed Lymphocyte Reaction (MLR) assay where dendritic cells and CD4+ cells from different donors are mixed in the presence of the mAb and stimulation of cytokine secretion is measured. According to particular embodiments, the methods for characterizing antibodies and antigen-binding fragments thereof that bind TIM-3 include those described below.

In another general aspect, the invention relates to a method of treating a cancer in a subject in need thereof, comprising administering to the subject a pharmaceutical composition of the invention. The cancer can, for example, be selected from but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

In another general aspect, the invention relates to a method of treating an infectious disease in a subject in need thereof, comprising administering to the subject a pharmaceutical composition of the invention.

In another general aspect, the invention relates to a method of treating an inflammatory disease in a subject in need thereof, comprising administering to the subject a pharmaceutical composition of the invention.

In another general aspect, the invention relates to a method of treating an autoimmune disease in a subject in need thereof, comprising administering to the subject a pharmaceutical composition of the invention.

In another general aspect, the invention relates to a method of treating a metabolic disease in a subject in need thereof, comprising administering to the subject a pharmaceutical composition of the invention.

According to embodiments of the invention, the pharmaceutical composition comprises a therapeutically effective amount of the anti-TIM-3 antibody or antigen-binding fragment thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-TIM-3 antibodies or antigen-binding fragments thereof, a therapeutically effective amount means an amount of the anti-TIM-3 antibody or antigen-binding fragment thereof that modulates an immune response in a subject in need thereof. Also as used herein with reference to anti-TIM-3 antibodies or antigen-binding fragments thereof, a therapeutically effective amount means an amount of the anti-TIM-3 antibody or antigen-binding fragment thereof that results in treatment of a disease, disorder, or condition; prevents or slows the progression of the disease, disorder, or condition; or reduces or completely alleviates symptoms associated with the disease, disorder, or condition.

According to particular embodiments, the disease, disorder or condition to be treated is cancer, preferably a cancer selected from the group consisting of a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CIVIL), a multiple myeloma (MM), an acute myeloid leukemia (AML), and other liquid tumors. According to other particular embodiments, the disease, disorder or condition to be treated is an infectious disease, an inflammatory disease, an immune disease, an autoimmune disease, and/or a metabolic disease.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, an infectious disease, disorder or condition, an immune disease, disorder or condition, an autoimmune disease, disorder or condition, an inflammatory disease, disorder or condition, and/or a metabolic disease, disorder or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, a composition used in the treatment of a cancer, an infectious disease, disorder or condition, an immune disease, disorder or condition, an autoimmune disease, disorder or condition, a metabolic disease, disorder or condition, and/or an inflammatory disease, disorder or condition can be used in combination with another treatment. For cancer treatment, the composition can be used in combination with another treatment including, but not limited to, a chemotherapy, an anti-CD20 mAb, an anti-CTLA-4 antibody, an anti-LAG-3 mAb, an anti-EGFR mAb, an anti-HER-2 mAb, an anti-CD19 mAb, an anti-CD33 mAb, an anti-CD73 mAb, an anti-CD47 mAb, an anti-DLL-3 mAb, an anti-apelin mAb, an anti-TIP-1 mAb, an anti-CLDN18.2 mAb, an anti-FOLR1 mAb, an anti-PD-L1 antibody, an anti-PD-1 antibody, a PD-1/PD-L1 therapy, other immuno-oncology drugs, an antiangiogenic agent, a radiation therapy, an antibody-drug conjugate (ADC), a targeted therapy, or other anticancer drugs.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of determining a level of TIM-3 in a subject, comprising (a) obtaining a sample from the subject; (b) contacting the sample with an antibody or antigen-binding fragment thereof of the invention; and (c) determining the level of TIM-3 in the subject. In certain embodiments, the sample is a tissue or blood sample. The tissue sample can, for example, be a cancer tissue sample. The blood sample can, for example, comprise cancer cells.

As used herein, "sample" refers to a biological sample isolated from a subject and can include, but is not limited to, whole blood, serum, plasma, blood cells, endothelial cells, tissue biopsies (e.g., a cancer tissue, a hepatic tissue, etc.), lymphatic fluid, ascites fluid, interstitial fluid, bone marrow, cerebrospinal fluid, saliva, mucous, sputum, sweat, urine, or any other secretion, excretion, or other bodily fluids. A "blood sample" refers to whole blood or any fraction thereof, including blood cells, serum, and plasma. A "blood sample" can, for example, comprise cancer cells.

In certain embodiments, the level of TIM-3 in the subject can be determined utilizing assays selected from, but not limited to, a Western blot assay, an ELISA assay, a FACS assay, and/or an immunohistochemistry (IHC). Relative protein levels can be determined by utilizing Western blot analysis, FACS assay, and immunohistochemistry (IHC), and absolute protein levels can be determined by utilizing an ELISA assay. When determining the relative levels of TIM-3, the levels of TIM-3 can be determined between at least two samples, e.g., between samples from the same subject at different time points, between samples from different tissues in the same subject, and/or between samples from different subjects. Alternatively, when determining absolute levels of TIM-3, such as by an ELISA assay, the absolute level of TIM-3 in the sample can be determined by creating a standard for the ELISA assay prior to testing the sample. A person skilled in the art would understand which analytical techniques to utilize to determine the level of TIM-3 in a sample from the subject utilizing the antibodies or antigen-binding fragments thereof of the invention.

Utilizing methods of determining a level of TIM-3 in a sample from a subject can lead to the diagnosis of abnormal (elevated, reduced, or insufficient) TIM-3 levels in a disease and making appropriate therapeutic decisions. Such a disease can be selected from, but not limited to, a cancer, preferably a cancer selected from the group consisting of lung cancer, gastric cancer, colon cancer, hepatocellular carcinoma, renal cell carcinoma, bladder urothelial carcinoma, metastatic melanoma, breast cancer, ovarian cancer, cervical cancer, head and neck cancer, pancreatic cancer, glioma, glioblastoma, and other solid tumors, and non-Hodgkin's lymphoma (NHL), acute lymphocytic leukemia (ALL), chronic lymphocytic leukemia (CLL), chronic myelogenous leukemia (CML), multiple myeloma (MM), acute myeloid leukemia (AML), and other liquid tumors, an inflammatory disease, an infectious disease, metabolic diseases, an immune disease, and/or an autoimmune disease.

EMBODIMENTS

The invention provides also the following non-limiting embodiments.

Embodiment 1 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of (1) SEQ ID NOs:43, 44, 169, 106, 107, and 170, respectively;
(2) SEQ ID NOs:55, 56, 57, 118, 119, and 120, respectively;
(3) SEQ ID NOs:58, 59, 60, 121, 122, and 123, respectively;
(4) SEQ ID NOs:61, 62, 63, 124, 125, and 126, respectively;
(5) SEQ ID NOs:64, 65, 66, 127, 128, and 129, respectively;
(6) SEQ ID NOs:67, 68, 69, 130, 131, and 132, respectively;
(7) SEQ ID NOs:70, 71, 72, 133, 134, and 135, respectively;
(8) SEQ ID NOs:73, 74, 75, 136, 137, and 138, respectively;
(9) SEQ ID NOs:76, 77, 78, 139, 140, and 141, respectively;
(10) SEQ ID NOs:79, 80, 81, 142, 143, and 144, respectively;
(11) SEQ ID NOs:82, 83, 84, 145, 146, and 147, respectively;
(12) SEQ ID NOs:85, 86, 87, 148, 149, and 150, respectively;
(13) SEQ ID NOs:88, 89, 90, 151, 152, and 153, respectively;
(14) SEQ ID NOs:91, 92, 93, 154, 155, and 156, respectively;
(15) SEQ ID NOs:94, 95, 96, 157, 158, and 159, respectively;
(16) SEQ ID NOs:97, 98, 99, 160, 161, and 162, respectively;
(17) SEQ ID NOs:100, 101, 102, 163, 164, and 165, respectively; or
(18) SEQ ID NOs:103, 104, 105, 166, 167, and 168, respectively;
wherein the antibody or antigen-binding fragment thereof specifically binds TIM-3, preferably human TIM-3.

Embodiment 2 is the isolated monoclonal antibody or antigen-binding fragment of embodiment 1, comprising a heavy chain variable region having a polypeptide sequence at least 95% identical to SEQ ID NO:1, 3, 5, 7, 9, 11, 13, 15, 17, 19, 21, 23, 25, 27, 29, 31, 33, 35, 37, 39, or 41 or a light chain variable region having a polypeptide sequence at least 95% identical to SEQ ID NO:2, 4, 6, 8, 10, 12, 14, 16, 18, 20, 22, 24, 26, 28, 30, 32, 34, 36, 38, 40, or 42.

Embodiment 3 is the isolated monoclonal antibody or antigen-binding fragment of embodiment 1 or 2, comprising
(a) a heavy chain variable region having the polypeptide sequence of SEQ ID NO:1, and a light chain variable region having the polypeptide sequence of SEQ ID NO:2;
(b) a heavy chain variable region having the polypeptide sequence of SEQ ID NO:3, and a light chain variable region having the polypeptide sequence of SEQ ID NO:4;
(c) a heavy chain variable region having the polypeptide sequence of SEQ ID NO:5, and a light chain variable region having the polypeptide sequence of SEQ ID NO:6;
(d) a heavy chain variable region having the polypeptide sequence of SEQ ID NO:7, and a light chain variable region having the polypeptide sequence of SEQ ID NO:8;
(e) a heavy chain variable region having the polypeptide sequence of SEQ ID NO:9, and a light chain variable region having the polypeptide sequence of SEQ ID NO:10;
(f) a heavy chain variable region having the polypeptide sequence of SEQ ID NO:11, and a light chain variable region having the polypeptide sequence of SEQ ID NO:12;
(g) a heavy chain variable region having the polypeptide sequence of SEQ ID NO:13, and a light chain variable region having the polypeptide sequence of SEQ ID NO:14;
(h) a heavy chain variable region having the polypeptide sequence of SEQ ID NO:15, and a light chain variable region having the polypeptide sequence of SEQ ID NO:16;
(i) a heavy chain variable region having the polypeptide sequence of SEQ ID NO:17, and a light chain variable region having the polypeptide sequence of SEQ ID NO:18;
(j) a heavy chain variable region having the polypeptide sequence of SEQ ID NO:19, and a light chain variable region having the polypeptide sequence of SEQ ID NO:20;
(k) a heavy chain variable region having the polypeptide sequence of SEQ ID NO:21, and a light chain variable region having the polypeptide sequence of SEQ ID NO:22;
(l) a heavy chain variable region having the polypeptide sequence of SEQ ID NO:23, and a light chain variable region having the polypeptide sequence of SEQ ID NO:24;
(m) a heavy chain variable region having the polypeptide sequence of SEQ ID NO:25, and a light chain variable region having the polypeptide sequence of SEQ ID NO:26;
(n) a heavy chain variable region having the polypeptide sequence of SEQ ID NO:27, and a light chain variable region having the polypeptide sequence of SEQ ID NO:28;
(o) a heavy chain variable region having the polypeptide sequence of SEQ ID NO:29, and a light chain variable region having the polypeptide sequence of SEQ ID NO:30;
(p) a heavy chain variable region having the polypeptide sequence of SEQ ID NO:31, and a light chain variable region having the polypeptide sequence of SEQ ID NO:32;
(q) a heavy chain variable region having the polypeptide sequence of SEQ ID NO:33, and a light chain variable region having the polypeptide sequence of SEQ ID NO:34;
(r) a heavy chain variable region having the polypeptide sequence of SEQ ID NO:35, and a light chain variable region having the polypeptide sequence of SEQ ID NO:36;
(s) a heavy chain variable region having the polypeptide sequence of SEQ ID NO:37, and a light chain variable region having the polypeptide sequence of SEQ ID NO:38;
(t) a heavy chain variable region having the polypeptide sequence of SEQ ID NO:39, and a light chain variable region having the polypeptide sequence of SEQ ID NO:40; or (u) a heavy chain variable region having the polypeptide sequence of SEQ ID NO:41, and a light chain variable region having the polypeptide sequence of SEQ ID NO:42.

Embodiment 4 is the isolated monoclonal antibody or antigen-binding fragment of any of embodiments 1 to 3, wherein the antibody or antigen-binding fragment thereof is chimeric.

Embodiment 5 is the isolated monoclonal antibody or antigen-binding fragment of any of embodiments 1 to 4, wherein the antibody or antigen-binding fragment thereof is human or humanized.

Embodiment 6 is the isolated monoclonal antibody or antigen-binding fragment of embodiment 5, wherein the antibody or antigen-binding fragment thereof comprises:
  (a) a heavy chain variable region having the polypeptide sequence of SEQ ID NO:171, and a light chain variable region having the polypeptide sequence of SEQ ID NO:175;
  (b) a heavy chain variable region having the polypeptide sequence of SEQ ID NO:172, and a light chain variable region having the polypeptide sequence of SEQ ID NO:175;
  (c) a heavy chain variable region having the polypeptide sequence of SEQ ID NO:173, and a light chain variable region having the polypeptide sequence of SEQ ID NO:176; or
  (d) a heavy chain variable region having the polypeptide sequence of SEQ ID NO:174, and a light chain variable region having the polypeptide sequence of SEQ ID NO:176.

Embodiment 7 is the isolated monoclonal antibody or antigen-binding fragment of any of embodiments 1 to 6, wherein the antibody or antigen-binding fragment thereof is capable of blocking binding of TIM-3 to phosphatidylserine (PtdSer), TIM-3 to galectin-9 (Gal-9), TIM-3 to carcinoembryonic antigen cell adhesion molecule 1 (CEACAM1), and/or TIM-3 to high mobility group protein B1 (HMGB1).

Embodiment 8 is an isolated nucleic acid encoding the monoclonal antibody or antigen-binding fragment of any of embodiments 1 to 7.

Embodiment 9 is a vector comprising the isolated nucleic acid of embodiment 8.

Embodiment 10 is a host cell comprising the vector of embodiment 9.

Embodiment 11 is a pharmaceutical composition, comprising the isolated monoclonal antibody or antigen-binding fragment of any of embodiments 1 to 7 and a pharmaceutically acceptable carrier.

Embodiment 12 is a method of blocking binding of TIM-3 to phosphatidylserine (PtdSer) in a subject in need thereof, comprising administering to the subject the pharmaceutical composition of embodiment 11.

Embodiment 13 is a method of blocking binding of TIM-3 to galectin-9 (Gal-9) in a subject in need thereof, comprising administering to the subject the pharmaceutical composition of embodiment 11.

Embodiment 14 is a method of blocking binding of TIM-3 to carcinoembryonic antigen cell adhesion molecule 1 (CEACAM1) in a subject in need thereof, comprising administering to the subject the pharmaceutical composition of embodiment 11.

Embodiment 15 is a method of blocking binding of TIM-3 to high mobility group protein B1 (HMGB1) in a subject in need thereof, comprising administering to the subject the pharmaceutical composition of embodiment 11.

Embodiment 16 is a method of treating cancer in a subject in need thereof, comprising administering to the subject the pharmaceutical composition of embodiment 11.

Embodiment 17 is a method of treating an infectious disease in a subject in need thereof, comprising administering to the subject the pharmaceutical composition of embodiment 11.

Embodiment 18 is a method of treating an inflammatory disease in a subject in need thereof, comprising administering to the subject the pharmaceutical composition of embodiment 11.

Embodiment 19 is a method of treating an autoimmune disease in a subject in need thereof, comprising administering to the subject the pharmaceutical composition of embodiment 11.

Embodiment 20 is a method of treating a metabolic disease in a subject in need thereof, comprising administering to the subject the pharmaceutical composition of embodiment 11.

Embodiment 21 is a method of producing the monoclonal antibody or antigen-binding fragment of any of embodiments 1 to 7, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or culture.

Embodiment 22 is a method of producing a pharmaceutical composition comprising the monoclonal antibody or antigen-binding fragment of any of embodiments 1 to 7, comprising combining the monoclonal antibody or antigen-binding fragment with a pharmaceutically acceptable carrier to obtain the pharmaceutical composition.

Embodiment 23 is a method of determining a level of TIM-3 in a subject, comprising (a) obtaining a sample from the subject; (b) contacting the sample with an antibody or antigen-binding fragment thereof of the invention; and (c) determining the level of TIM-3 in the subject.

Embodiment 24 is the method of embodiment 23, wherein the sample is a tissue sample.

Embodiment 25 is the method of embodiment 24, wherein the tissue sample is a cancer tissue sample.

Embodiment 26 is the method of embodiment 23, wherein the sample is a blood sample.

EXAMPLES

Example 1

Identification of Anti-TIM-3 Monoclonal Antibodies

Mice were immunized with Fc-tagged human and cynomolgus TIM-3 extracellular domain (ECD) proteins and adjuvant. Plasma titer was determined by enzyme linked immunosorbent assay (ELISA). After euthanization, spleens and lymph nodes were collected to produce hybridomas. Hybridomas were grown in 384-well tissue culture plates and supernatants from individual wells were screened by ELISA to identify positive binders for human and cynomolgus TIM-3 ECD proteins. Positive supernatants were also screened for blocking of phosphatidylserine binding to TIM-3 recombinant protein and binding to native TIM-3 protein by FACS analysis on TIM-3-expressing HEK293 cells. Positive clones were isolated and sequenced.

Sequences of heavy and light chain variable regions for anti-TIM-3 monoclonal antibodies are provided in Tables 1 and 2, and the CDR regions for the anti-TIM-3 monoclonal antibodies are provided in Tables 3 and 4. The CDR regions for the anti-TIM-3 monoclonal antibodies were determined utilizing the IMGT method.

TABLE 1

Sequences of heavy chain variable regions for anti-TIM-3 monoclonal antibodies (mAbs)

| mAb clones | VH |
|---|---|
| 20-L10-A | QIQLVQSGPELKKPGETVKISCKASGYTFTNYGMNWVKQAPGKVLKWMVWIN TYTGEPTYADDFKGRFAFSLETSASTAYLQINNLKNEDTATYFCARDAMDYWG QGTSVTVSS (SEQ ID NO: 1) |
| 15-L23-A | QIQLVQSGPELKKPGETVKISCRASGYTFTNYGMNWVKQAPGKGLKWMVWIN TYTGEPTFADDFKGRFAFSLETSASTAYLQIINLKNEDTATYFCARDTMDYWGQ GTSVTVSS (SEQ ID NO: 3) |
| 8-F3-A | QIQLVQSGPELKKPGETVKISCKASGYTFTNYGMNWVKQAPGKGLKWMAWIN TYTGEPTYADDFKGRFAFSLETSASTAYLQINNLKNEDTATYFCARDLEDYWGQ GTTLTVSS (SEQ ID NO: 5) |
| 7-P15-A | QIQLVQSGPELKKPGETVKISCKASGYTFTNYGMNWVKQAPGKGLKWMGWIN TYTGEPTYADDFKGRFAFSLETSASTAYLQINNLKNEDTATYFCARDLMDYWG QGTTLTVSS (SEQ ID NO: 7) |
| 18-N1-A | QVQLQQPGAELVRPGVSVKLSCKASGYTFTSYWMHWIKQRPEQGLERIGEINPS NGGTNYNEKFKNKATLTVDKSSSTAYMQLSSLTSEDSAVYYCARSYYTYDAID YWGQGTSVTVSS (SEQ ID NO: 9) |
| 18-O22-A | EVQLQQSGPELVKPGASVKVSCKASGYTFTSYVMHWVKQKPGQGLEWIGYINP YNDVTKYNEKFKGKATLTSDKSSTAYMELSSLTSEDSAVYYCARSSDYDDGH WYFDVWGAGTTVTVSS (SEQ ID NO: 11) |
| 16-L3-A | QVQLQQSGPELVKPGASVKMSCKASGYTFTSYYIHWVKQRPGQGLEWIGWIYP GDGSTKYNEKFKGKTTLTADKSSSTAYMLLSSLTSEDSAIYFCATDRYDVAYWG QGTLVTVSA (SEQ ID NO: 13) |
| 16-K5-A | QVQLQQSGAELVKPGASVKLSCKASGYTFTSSDINWVRQRPEQGLEWIGWIFPG DGSTKYNEKFKGKATLTTDKSSSTAYMQLSRLTSEDSAVYFCARGLDYWGQGT TLTVSS (SEQ ID NO: 15) |
| 19-A14-A | DVQLQGSGPGLVKPSQSLSLTCTVTGYSITSDYAWNWIRQFPGNILEWMGYISYS GSTSYNPSLKSRISITRDTSKNQFFLQLNSVTTEDTATYYCARDGRYDYYAMDY WGQGTSVTVSS (SEQ ID NO: 17) |
| 2-K2-A | QVQLQQSGAELAKPGASVKMSCKASGYTFTTYWMHWVKQRPGQGLEWIGYIN PSTGYTEYNQKFKDKSTLTADKSSSTAYMQLSSLTSEDSAVYYCANDHEGGFAY WGQGTLVTVSA (SEQ ID NO: 19) |
| 6-H6-A | EVQLQQFGAELVKPGASVKISCKASGYTFTDYNMDWVKQSHGKSLEWIGDIDP NYDSTTYNQKFKGKATLTVDKSSSTAYMELRSLTSEDTAVYYCARGGHYRYDG YYAMDYWGQGTSVTVSS (SEQ ID NO: 21) |
| 1-A19-A | EVQLQQFGAELVKPGASVKISCKASGYTFTDYNMDWVKQSHGKSLEWIGDIDP NYDITTYNQKFKGKATLTVDKSSSTAYMELRSLTSEDTAVYYCARGGHYRYDG YYALDYWGQGTSVTVSS (SEQ ID NO: 23) |
| 10-O15-A | QVQLQQSGADLVRPGASVKLSCKALGYTFTDYEMHWVKQTPVHGLEWIGAIHP GSGGTAYNQKFKGKATLTADKSSSTAYMELSSLTSEDSAVYFCSRSYYRYTGYF DVWGAGTTVTVSS (SEQ ID NO: 25) |
| 6-I13-A | EVQLQQSGPELEKPGASVKISCKASGYSFTGYNMNWVKQSNGKSLEWIGNIDPY YGVTSYNQKFKGKATLTVDKSSSTAYMQLKSLTSEDSAVYYCASYSLTYDGYY PFAYWGQGTLVTVSA (SEQ ID NO: 27) |
| 5-K4-A | EVQLQQSGPELVKTGASVKISCKASGYSFTAYYIHWVKQSHGKSLEWIGHISCFN GATSYNQKFKGKATFTVDTSSSTAYMQFNSLTSEDSAVYYCARRGDFDRPEFAY WGQGTLVTVSA (SEQ ID NO: 29) |
| 12-G18-A | DVQLQESGPGLVKPSQSLSLTCTVTGYSITSDYAWNWIRQFPGNKLEWMGYISY SGSTSYNPSLKSRISITRDTSKNQFFLQLNSVTIGDTATYYCASNYRYDYWFFGV WGAGTTVTVSS (SEQ ID NO: 31) |
| 10-M21-A | DVQLQESGPTLVKPSQTLSLTCSVTGDSITSGYWNWIRKFPGNKLEYMGYISYSG STYYNPSLKSRISIIRDTSKNQYYLQLNSVTTEDTATYYCVSGNHFDYWGQGTTL TVSS (SEQ ID NO: 33) |
| 12-M11-A | SQVQLQQSGAELAKPGASVKMSCKASGYFTSYWMHWVKQRPGQGLEWIGYIN PITGYTEYNQKFKDKATLTADKSSSTAYMQLSRLTSEDSAVYYCARGVENFDYL YAMDYWGQGASVTVSS (SEQ ID NO: 35) |
| 5-C11-A | EVQLVESGGGLVKPGGSLKLSCAASGFTFSDFYMYWVRQTPEKRLEWVATISD GGSYTYYPDSVKGRFTISRDNAKNNLYLQMSSLKSEDTAMYYCASGYYYGSDY VMDYWGQGTSVTVSS (SEQ ID NO: 37) |

TABLE 1-continued

Sequences of heavy chain variable regions for anti-TIM-3 monoclonal antibodies (mAbs)

mAb clones  VH

16-J5-A   DVQLVESGGGLVQPGGSRKLSCAASGFTFSSFGMNWVRQAPEKGLEWVAYISS
          GSSTIYYADTVKGRFTISRDNPKNTLFLQMTSLRSEDTAMYYCARWGRWADFD
          YWGQGTTLTVSS (SEQ ID NO: 39)

7-N2-A    QVQLKESGPGLVAPSQSLSITCTVSGFSLTGFGVNWVRQPPGKGLEWLGMIWGD
          GSTDYNSTLKSRLSISKDNSKSQVFLKMNSLQTDDTARYYCARDYYGYVGNAM
          DYWGQGTSVTVSS (SEQ ID NO: 41)

VH: heavy chain variable region

TABLE 2

Sequences of light chain variable regions for anti-TIM-3 mAbs mAb clones  VL

20-L10-A   DVVMTQTPLSLPVSLGDQASISCRSSQSLVHSNGNTYLHWYLQKPGQSPKLLIY
           KVSNRFSGVPDRFSGSGSGTDFTLKISRVEAEDLGVYFCSQNTHVPWTFGGGTK
           LEIK (SEQ ID NO: 2)

15-L23-A   DIVMTQTPLSLPVSLGDQASISCRSSQSLVHSNGNTYLHWYLQKPGQSPKLLIYK
           VSNRFSGVPDRFSGSGSGTDFTLKISRVEAEDLGVYFCSQNTHVPWTFGGGTKLE
           IK (SEQ ID NO: 4)

8-F3-A     DVVMTQTPLSLPVSLGDQASISCRSSQSLVHSNGNTYLHWYLQKPGQSPKLLIY
           KVSNRFSGVPDRFSGSGSGTDFTLKISRVEAEDLGVYFCSQTTHVPWTFGGGTKL
           EIK (SEQ ID NO: 6)

7-P15-A    DVVMTQTPLSLPVSLGDQASISCRSSQSLVHSNGNTYLHWYLQKPGQSPKLLIY
           KVSNRFSGVPDRFSGSGSGTDFTLKITRVEAEDLGVYFCSQSIHVPYTFGGGTKL
           EIK (SEQ ID NO: 8)

18-N1-A    DIVMSQSPSSLAVSAGEKVTMSCKSSQSLLNSRTRKNYLAWYQQKPGQSPKLLI
           YWASTRESGVPDRFTGSGSGTDFTLTISSVQAEDLAVYYCKQSYNLYTFGGGTK
           LEIK (SEQ ID NO: 10)

18-O22-A   DIVLTQSPASLAVSLGQRATISCKASQSVDYDGESYMNWYQQKPGQPPKLLIYV
           ASNLESGIPVRFSGSGSGTDFTLNIHPVEEEDAATYYCQQSNEDPTWTFGGGTKL
           EIK (SEQ ID NO: 12)

16-L3-A    EIVLTQSPALMAASPGEKVTITCSVSSSISSSNLHWYQQKSETSPKPWIYGTSNLA
           S GVPVRFSGSGSGTSYSLTISSMEAEDAATYYCQQWSSYPLTFGAGTKLELK
           (SEQ ID NO: 14)

16-K5-A    DIKMTQSPSSMYASLGERVTITCKASQDINSYLGWFQQKPGKSPKTLIYRADRLV
           DGVPSRFSGSGSGQDYSLTISSLEYEDMGIYYCLQYDEFPLTFGAGTKLELK
           (SEQ ID NO: 16)

19-A14-A   DIVLTQSPASLAVSLGQRATISCRASESVDNYGISFMNWFQQKPGQPPKLLIFAAS
           NQGSGVPARFSGSGSGTDFSLNIHPMEEDDTAMYFCHQSKEVPWTFGGGTKLEI
           K (SEQ ID NO: 18)

2-K2-A     DILMTQSPSSMSVSLGDTVSITCHASQGISSNIGWLQQKPGKSFKGLIYHGTNLED
           GVPSRFSGSGSGADYSLTISSLESEDFADYYCVQYAQFPFTFGSGTKLEIK (SEQ
           ID NO: 20)

6-H6-A     DIVLTQSPASSAVSLGQRATFSCRASQSVSTSSYSFMHWYQQKPGQPPKLLIKYA
           SNLESGVPARFSGSGSGTDFTLNIHPVEEEDTATYYCQHSWEIPPTFGGGTNLEIK
           (SEQ ID NO: 22)

1-A19-A    DIVLTQSPASLAVSLGQRATISCKASQSVDYDGDSYMNWYQQKPGQPPKLLIYA
           ASNLESGIPARFSGSGSGTDFTLNIHPVEEEDAATYYCQQSNEDPFTFGSGTKLEI
           K (SEQ ID NO: 24)

10-O15-A   DIVLTQSPASLAVSLGQRATISCRASKSVSASGYSMHWYQQKPGQPPKWYLA
           SNLESGVPARFSGSGSGTDFTLNVHPVEEEDAATYYCQHSRELPFTFGGGTKLEI
           K (SEQ ID NO: 26)

TABLE 2-continued

Sequences of light chain variable regions for anti-TIM-3 mAbs

| mAb clones | VL |
|---|---|
| 6-I13-A | DIVLTQSPASLAVSLGQRATISCRASKSVSTSGYSYMHWYQQKPGQPPKLLIYLA SNLESGVPARFSGSGSGTDFTLNIHPVEEEDAATYYCQHSRELPYTFGGGTKLEI K (SEQ ID NO: 28) |
| 5-K4-A | DIVLTQSPASLAVSLGQRATISCRASESVEYYGTSLMQWYQQKPGQPPKLLIYAA SNVESGVPARFSGSGSGTDFSLNIHPVEEDDIAMYFCQQSRKVPWTFGGGTKLEI K (SEQ ID NO: 30) |
| 12-G18-A | DIVLTQSPASLAVSLGQRATISCRASESVDNYGISFMNWFQQKPGQPPKLLIYAES NQGSGVPARFSGSGSGTDFSLNIHPMEEDDTAMYFCQQSKEVPYTFGGGTKLEI K (SEQ ID NO: 32) |
| 10-M21-A | DIQMTQSPSSLSASLGGKVTITCKASQDINRYIAWYQHKPGKGPRLLIHYTSTLQP GIPSRFSGSGSGRDYSFSISNLEPEDIATYYCLQYDNLLFTFGSGTKLEIK (SEQ ID NO: 34) |
| 12-M11-A | QIVLTQSPAIMSASPGEKVTMTCSASSSISYMHWYQQKPGTSPKRWIYDTSKLAS GVPTRFNGSGSGTSYSLTISSMEAEDAATYYCHQRSSYRTFGGGTKLEIK (SEQ ID NO: 36) |
| 5-C11-A | DIVMSQSPSSLAVSAGEKVTMSCKSSQSLLNSRTRKNYLAWYQQKPGQSPKLLI YWASTRESGVPDRFTGSGSGTDFTLTISSVQADDLAVYYCKQSYNLLTFGAGTK LELK (SEQ ID NO: 38) |
| 16-J5-A | DIVLTQSPASLAVSLGQRATISCKASQSVDYDGDSYMNWYQQKPGQPPKLLIYA ASNLESGIPARFSGSGSGTDFTLNIHPVEEEDAATYYCQQSNEDPPTFGGGTKLEI K (SEQ ID NO: 40) |
| 7-N2-A | DIVMSQSPSSLAVSAGEKVTMSCKSSQSLLNSRTRKNYLAWYQQKPGQSPKLLI YWASTRESGVPDRFTGSGSGTDFTLTISSVQAEDLAVYYCKQSYNHMYTFGGGT KLEIK (SEQ ID NO: 42) |

VL: light chain variable region

TABLE 3

CDR Regions 1-3 of heavy chain for anti-TIM-3 mAbs

| | HC | | |
|---|---|---|---|
| mAb clones | CDR1 (SEQ ID NO:) | CDR2 (SEQ ID NO:) | CDR3 (SEQ ID NO:) |
| 20-L10-A | GYTFTNYG (43) | INTYTGEP (44) | ARDAMDY (45) |
| 15-L23-A | GYTFTNYG (46) | INTYTGEP (47) | ARDTMDY (48) |
| 8-F3-A | GYTFTNYG (49) | INTYTGEP (50) | ARDLEDY (51) |
| 7-P15-A | GYTFTNYG (52) | INTYTGEP (53) | ARDLMDY (54) |
| 18-N1-A | GYTFTSYW (55) | INPSNGGT (56) | ARSYYTYDAIDY (57) |
| 18-O22-A | GYTFTSYV (58) | INPYNDVT (59) | ARSSDYDDGHWYFDV (60) |
| 16-L3-A | GYTFTSYY (61) | IYPGDGST (62) | ATDRYDVAY (63) |
| 16-K5-A | GYTFTSSD (64) | IFPGDGST (65) | ARGLDY (66) |
| 19-A14-A | GYSITSDYA (67) | ISYSGST (68) | ARDGRYDYYAMDY (69) |
| 2-K2-A | GYTFTTYW (70) | INPSTGYT (71) | ANDHEGGFAY (72) |
| 6-H6-A | GYTFTDYN (73) | IDPNYDST (74) | ARGGHYRYDGYYAMDY (75) |
| 1-A19-A | GYTFTDYN (76) | IDPNYDIT (77) | ARGGHYRYDGYYALDY (78) |
| 10-O15-A | GYTFTDYE (79) | IHPGSGGT (80) | SRSYYRYTGYFDV (81) |
| 6-I13-A | GYSFTGYN (82) | IDPYYGVT (83) | ASYSLTYDGYYPFAY (84) |

TABLE 3-continued

CDR Regions 1-3 of heavy chain for anti-TIM-3 mAbs

| mAb clones | HC CDR1 (SEQ ID NO:) | CDR2 (SEQ ID NO:) | CDR3 (SEQ ID NO:) |
|---|---|---|---|
| 5-K4-A | GYSFTAYY (85) | ISCFNGAT (86) | ARRGDFDRPEFAY (87) |
| 12-G18-A | GYSITSDYA (88) | ISYSGST (89) | ASNYRYDYWFFGV (90) |
| 10-M21-A | GDSITSGY (91) | ISYSGST (92) | VSGNHFDY (93) |
| 12-M11-A | GYFTSYW (94) | INPITGYT (95) | ARGVENFDYLYAMDY (96) |
| 5-C11-A | GFTFSDFY (97) | ISDGGSYT (98) | ASGYYYGSDYVMDY (99) |
| 16-J5-A | GFTFSSFG (100) | ISSGSSTI (101) | ARWGRWADFDY (102) |
| 7-N2-A | GFSLTGFG (103) | IWGDGST (104) | ARDYYGYVGNAMDY (105) |

HC: heavy chain;
CDR: complementarity determining region
The HC CDRs for the anti-TIM-3 mAbs were determined utilizing the IMGT method (Lefranc, M.-P. et al., Nucleic Acids Res. 1999; 27: 209-212).

TABLE 4

CDR regions 1-3 of the light chain for anti-TIM-3 mAbs

| mAb clones | LC CDR1 (SEQ ID NO:) | CDR2 (SEQ ID NO:) | CDR3 (SEQ ID NO:) |
|---|---|---|---|
| 20-L10-A | QSLVHSNGNTY (106) | KVS (107) | SQNTHVPWT (108) |
| 15-L23-A | QSLVHSNGNTY (109) | KVS (110) | SQNTHVPWT (111) |
| 8-F3-A | QSLVHSNGNTY (112) | KVS (113) | SQTTHVPWT (114) |
| 7-P15-A | QSLVHSNGNTY (115) | KVS (116) | SQSIHVPYT (117) |
| 18-N1-A | QSLLNSRTRKNY (118) | WAS (119) | KQSYNLYT (120) |
| 18-O22-A | QSVDYDGESY (121) | VAS (122) | QQSNEDPTWT (123) |
| 16-L3-A | SSISSSN (124) | GTS (125) | QQWSSYPLT (126) |
| 16-K5-A | QDINSY (127) | RAD (128) | LQYDEFPLT (129) |
| 19-A14-A | ESVDNYGISF (130) | AAS (131) | HQSKEVPWT (132) |
| 2-K2-A | QGISSN (133) | HGT (134) | VQYAQFPFT (135) |
| 6-H6-A | QSVSTSSYSF (136) | YAS (137) | QHSWEIPPT (138) |
| 1-A19-A | QSVDYDGDSY (139) | AAS (140) | QQSNEDPFT (141) |
| 10-O15-A | KSVSASGYSY (142) | LAS (143) | QHSRELPFT (144) |
| 6-I13-A | KSVSTSGYSY (145) | LAS (146) | QHSRELPYT (147) |
| 5-K4-A | ESVEYYGTSL (148) | AAS (149) | QQSRKVPWT (150) |
| 12-G18-A | ESVDNYGISF (151) | AES (152) | QQSKEVPYT (153) |
| 10-M21-A | QDINRY (154) | YTS (155) | LQYDNLLFT (156) |
| 12-M11-A | SSISY (157) | DTS (158) | HQRSSYRT (159) |
| 5-C11-A | QSLLNSRTRKNY (160) | WAS (161) | KQSYNLLT (162) |
| 16-J5-A | QSVDYDGDSY (163) | AAS (164) | QQSNEDPPT (165) |
| 7-N2-A | QSLLNSRTRKNY (166) | WAS (167) | KQSYNHMYT (168) |

LC: light chain;
CDR: complementarity determining region
The LC CDRs for the anti-TIM-3 mAbs were determined utilizing the IMGT method (Lefranc, M.-P. et al., Nucleic Acids Res. 1999; 27: 209-212).

Example 2

TIM-3 and PtdSer Binding Assay Using ELISA

To determine the effect of anti-TIM-3 antibodies on the interaction of TIM-3 with phosphatidylserine (PtdSer), 384-well ELISA plates were coated with PtdSer or phosphatidylcholine (PtdChol) at room temperature. The wells were washed using PBS supplemented with 0.1% Tween-20 and then blocked using PBS supplemented with 2% bovine serum albumin (BSA). Plates were washed and then incubated with a pre-equilibrated mixture of purified antibodies (0, 0.03, 0.08, 0.25, 0.74, 2.22, 6.67, or 20 µg/mL mAb) and TIM3(ECD)-huFc, a fusion protein containing the extracellular domain (ECD) of human TIM-3 and human Fc (huFc), in blocking buffer supplemented with $CaCl_2$. The plates were washed and then incubated with HRP-coupled anti-huFc secondary antibody. Plates were washed, incubated with an HRP substrate, and read using a POLARstar Omega Microplate (BMG LABTECH). The assay was performed in triplicate. The signal of TIM-3 binding to PtdSer was defined as 100% signal and the signal of TIM-3 binding to PtChol as zero (background) to set the assay window. Results of the inhibition of human TIM-3 binding to PtdSer by anti-TIM-3 monoclonal antibodies (mAbs) as demonstrated by the ELISA assays are shown in FIGS. 1A-1F.

Example 3

FACS Binding Analysis of Purified Antibodies

Figure 2:
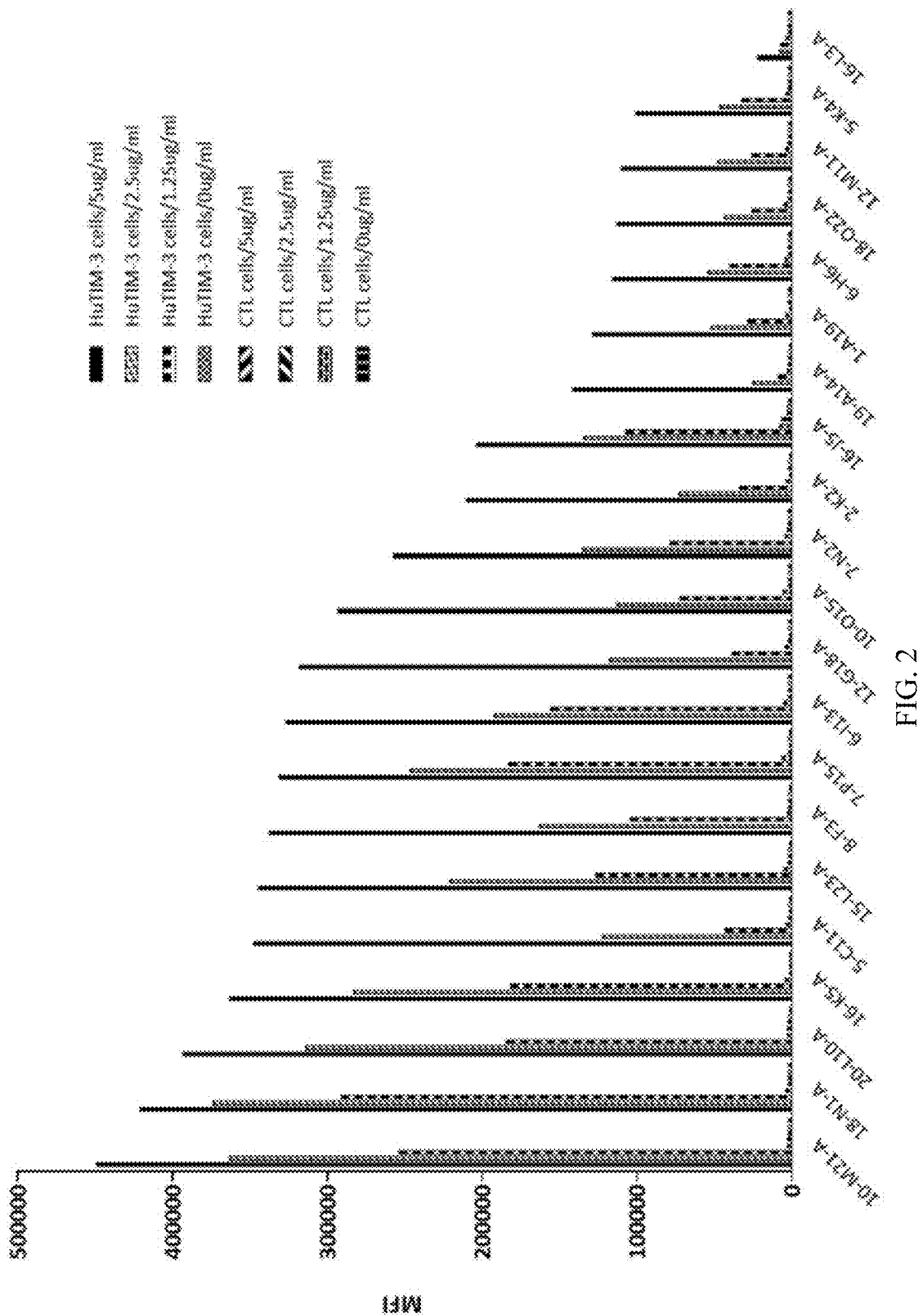
FIG. 2 shows FACS binding analysis of anti-TIM-3 mAbs. The binding of purified anti-TIM-3 mAbs to HEK293 cells transiently transfected with human TIM-3 (labeled as "HuTIM-3 cells") or parental HEK293 cells (labeled as "CTL cells") was tested by FACS at 3 different concentrations. An anti-mouse secondary Ab AlexaFluor488 was used for detection.

A human TIM-3-expressing plasmid was made and transiently transfected into HEK293T cells. After approximately 48 hours, cells were transferred to a 384-well V-bottom plate. Cells were washed with ice-cold FACS buffer (PBS supplemented with 1% BSA) and incubated with purified mAbs with gentle agitation at 4° C. for 45 minutes. The cells were washed with FACS buffer and incubated with an anti-mouse secondary Ab AlexaFluor488. The cells were washed and analyzed by FACS. Results of the FACS binding analysis of the anti-TIM-3 mAbs are provided in FIG. 2.

Example 4

Dissociation Constant (KD) Analysis

Binding experiments were performed on OCTET Red96 at 25° C. Antibodies were loaded onto Anti-Mouse Fc (AMC) biosensors. Loaded sensors were dipped into serial dilutions of antigen. Kinetic constants were calculated using a monovalent (1:1) model. The assay buffer was PBS supplemented with 0.1% BSA, 500 mM NaCl, 0.02% Tween-20, pH 7.2. The dissociation constant for antibody-antigen binding was determined for the anti-TIM-3 monoclonal antibodies and is shown below in Table 5.

TABLE 5

KD values for anti-TIM-3 mAbs

| mAb clones | KD (nM) Human TIM-3 | KD (nM) Cyno TIM-3 |
|---|---|---|
| 5-K4-A | 1.8 | 6.7 |
| 16-J5-A | 2.7 | 0.054 |
| 10-O15-A | 3.1 | 2.9 |
| 18-N1-A | 1.1 | 14 |
| 16-K5-A | 7.9 | 6.4 |
| 6-I13-A | 9.9 | 5.2 |
| 10-M21-A | 16 | 7.5 |
| 16-L3-A | 14 | 6.5 |
| 1-A19-A | 2.2 | 2.8 |
| 15-L23-A | 13 | 8.9 |
| 20-L10-A | 10 | 4.1 |
| 8-F3-A | 1.6 | 22 |

Example 5

Humanization of Anti-TIM-3 mAb

The mouse anti-TIM-3 mAb 16-K5-A was humanized to reduce the potential of immunogenicity when used in human patients. The sequences of the variable regions of the heavy and light chains (VH and VL) were compared with the human antibody sequences in the Protein Data Bank (PDB) database and homology models were built by applying SWISS-modeling. The CDRs in both the heavy and light chains of the mouse mAbs were grafted into human frameworks that have the highest possibility of maintaining the proper structure likely required for antigen binding. Back-mutations from human residues to mouse residue were designed when necessary. The sequences of the humanized VH and VL regions are shown in Table 6. The humanized VH and VL regions were fused to the constant regions of human IgG4 heavy chain and kappa light chain, respectively. Constructs corresponding to the mAb sequences were used for transient transfection in 293E cells. The resulting antibody was purified by Protein A affinity column.

TABLE 6

Sequences of heavy chain and light chain variable regions of humanized anti-TIM-3 mAbs

| VH/VL | SEQUENCE | SEQ ID NO: |
|---|---|---|
| H1 | EVQLVESGGGLVQPGGSLRLSCAASGYTFTSSDINWVRQAPGKG LVWIGWIFPGDGSTKYTPSLKDQATLSTDKAKNTAYLQMNSLRA EDTAVYFCARGLDYWGQGTLVTVSS | 171 |
| H2 | EVQLVESGGGLVQPGGSLRLSCAASGYTFTSSDINWVRQAPGKG LVWIGWIFPGDGSTKYTPSLKDQATLSTDLAKNTAYLQMNSLRA EDTAVYFCARGLDYWGQGTLVTVSS | 172 |
| H5 | QVQLQESGPGLVKPSETLSLTCTASGYTFTSSDINWVRQPPGKG LEWIGWIFPGDGSTKYNPSLKSRATLSTDKSKNQASLNLDSVSA ADTAIYFCARGLDYWGKGSTVTVSS | 173 |
| H7 | QVQLQESGPGLVKPSETLSLTCKASGYTFTSSDINWVRQPPGKG LEWIGWIFPGDGSTKYNPSLKSRATLSTDKSKNQASLNLSSVTA ADTAVYFCARGLDYWGKGTTVTVSS | 174 |
| L1 | DIQMTQSPSSLSASVGDRVTITCKASQDINSYLGWFQQKPGKAP KTLIYRADRLVDGVPSRFSGSGSGQDYTFTISSLQPEDIATYYC LQYDEFPLTFGQGTKLEIK | 175 |
| L5 | DIQMTQSPSSLSASVGDRVTITCKASQDINSYLGWFQQKPGKAP KTLIYRADRLVDGVPSRFSGSGSGQDYTFTISSLQPEDIATYYC LQYDEFPLTFGPGTKVDIK | 176 |

H1, H2, H5 and H7 are humanized VH sequences; L1 and L5 are humanized VL sequences. H1L1, H2L1, H5L5 and H7L5 refer to the humanized mAbs constructed using a specific VH (e.g., H1) and a specific VL (e.g., L1) combination (to produce H1L1).

Example 6

ELISA Binding Analysis for Chimeric and Humanized Anti-TIM-3 mAbs

Figure 3A:
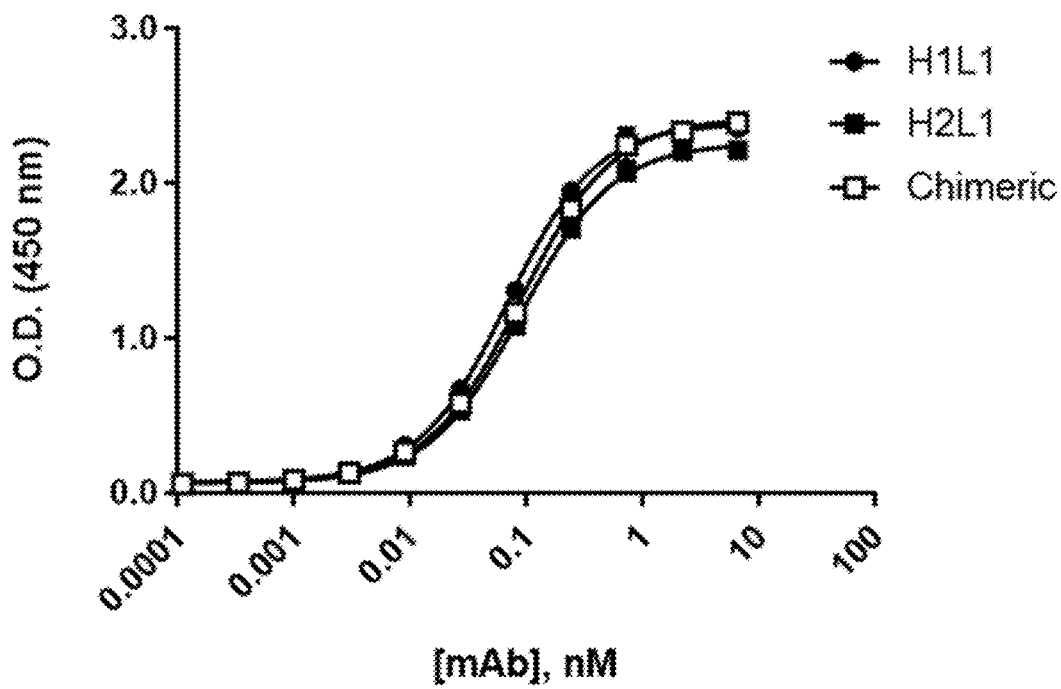
FIGS. 3A and 3B show the result of binding of chimeric and humanized versions of mAb 16-K5-A to recombinant human TIM-3(ECD)-6His immobilized on a plate in an ELISA assay.
Figure 3B:
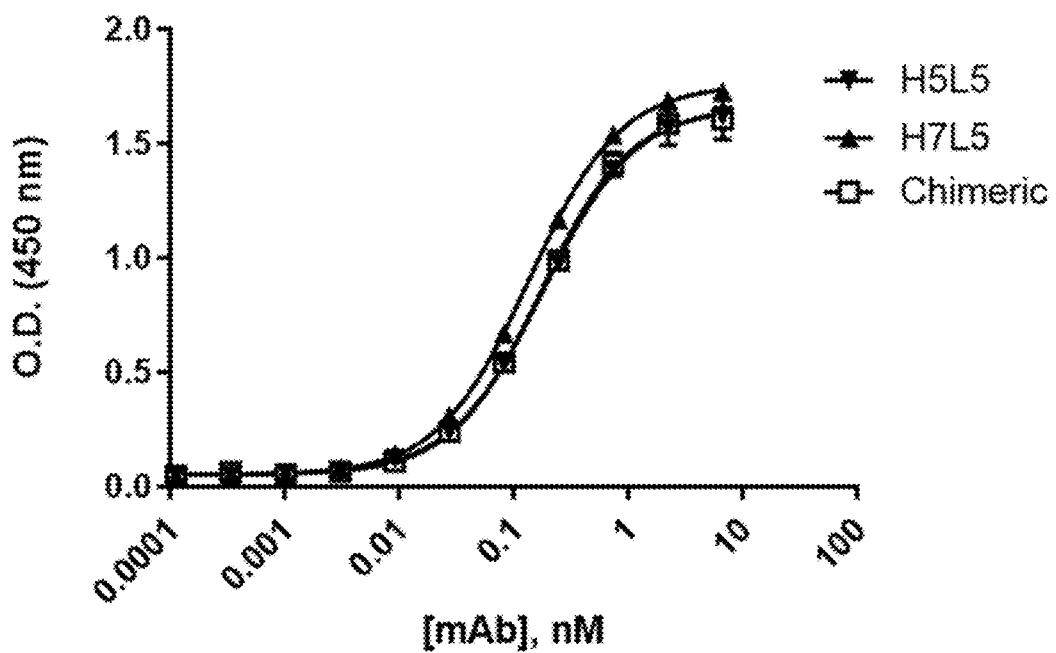

Recombinant human TIM-3(ECD)-6His in carbonate coating buffer was coated on an ELISA plate at 4° C. overnight. The chimeric and humanized versions of anti-TIM-3 mAbs (H1L1, H2L1, H5L5 and H7L5) were added to the plate at different concentrations after being washed and incubated for 1 hour at room temperature. The plate was washed and antibody-binding was detected by adding anti-human IgG conjugated to horseradish peroxidase (hIgG-HRP) (ThermoFisher Scientific, Cat#: 31410) and incubating for 60 minutes. After washing, the ELISA was developed using One-step Detection Solution (ThermoFisher Scientific, Cat #: 34028), which was measured as the absorbance at 450 nm. Results are shown in FIGS. 3A and 3B.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. An isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of:
   (1) SEQ ID NOs:43, 44, 169, 106, 107, and 170, respectively;
   (2) SEQ ID NOs:55, 56, 57, 118, 119, and 120, respectively;
   (3) SEQ ID NOs:58, 59, 60, 121, 122, and 123, respectively;
   (4) SEQ ID NOs:61, 62, 63, 124, 125, and 126, respectively;
   (5) SEQ ID NOs:64, 65, 66, 127, 128, and 129, respectively;
   (6) SEQ ID NOs:67, 68, 69, 130, 131, and 132, respectively;
   (7) SEQ ID NOs:70, 71, 72, 133, 134, and 135, respectively;

(8) SEQ ID NOs:73, 74, 75, 136, 137, and 138, respectively;
(9) SEQ ID NOs:76, 77, 78, 139, 140, and 141, respectively;
(10) SEQ ID NOs:79, 80, 81, 142, 143, and 144, respectively;
(11) SEQ ID NOs:82, 83, 84, 145, 146, and 147, respectively;
(12) SEQ ID NOs:85, 86, 87, 148, 149, and 150, respectively;
(13) SEQ ID NOs:88, 89, 90, 151, 152, and 153, respectively;
(14) SEQ ID NOs:91, 92, 93, 154, 155, and 156, respectively;
(15) SEQ ID NOs:94, 95, 96, 157, 158, and 159, respectively;
(16) SEQ ID NOs:97, 98, 99, 160, 161, and 162, respectively;
(17) SEQ ID NOs:100, 101, 102, 163, 164, and 165, respectively; or
(18) SEQ ID NOs:103, 104, 105, 166, 167, and 168, respectively;
wherein the antibody or antigen-binding fragment thereof specifically binds TIM-3.

2. The isolated monoclonal antibody or antigen-binding fragment of claim 1, comprising a heavy chain variable region having a polypeptide sequence at least 95% identical to SEQ ID NO:1, 3, 5, 7, 9, 11, 13, 15, 17, 19, 21, 23, 25, 27, 29, 31, 33, 35, 37, 39, 41, 171, 172, 173, or 174, or a light chain variable region having a polypeptide sequence at least 95% identical to SEQ ID NO:2, 4, 6, 8, 10, 12, 14, 16, 18, 20, 22, 24, 26, 28, 30, 32, 34, 36, 38, 40, 42, 175, or 176.

3. The isolated monoclonal antibody or antigen-binding fragment of claim 1, comprising:
a. a heavy chain variable region having the polypeptide sequence of SEQ ID NO:1, and a light chain variable region having the polypeptide sequence of SEQ ID NO:2;
b. a heavy chain variable region having the polypeptide sequence of SEQ ID NO:3, and a light chain variable region having the polypeptide sequence of SEQ ID NO:4;
c. a heavy chain variable region having the polypeptide sequence of SEQ ID NO:5, and a light chain variable region having the polypeptide sequence of SEQ ID NO:6;
d. a heavy chain variable region having the polypeptide sequence of SEQ ID NO:7, and a light chain variable region having the polypeptide sequence of SEQ ID NO:8;
e. a heavy chain variable region having the polypeptide sequence of SEQ ID NO:9, and a light chain variable region having the polypeptide sequence of SEQ ID NO:10;
f. a heavy chain variable region having the polypeptide sequence of SEQ ID NO:11, and a light chain variable region having the polypeptide sequence of SEQ ID NO:12;
g. a heavy chain variable region having the polypeptide sequence of SEQ ID NO:13, and a light chain variable region having the polypeptide sequence of SEQ ID NO:14;
h. a heavy chain variable region having the polypeptide sequence of SEQ ID NO:15, and a light chain variable region having the polypeptide sequence of SEQ ID NO:16;
i. a heavy chain variable region having the polypeptide sequence of SEQ ID NO:17, and a light chain variable region having the polypeptide sequence of SEQ ID NO:18;
j. a heavy chain variable region having the polypeptide sequence of SEQ ID NO:19, and a light chain variable region having the polypeptide sequence of SEQ ID NO:20;
k. a heavy chain variable region having the polypeptide sequence of SEQ ID NO:21, and a light chain variable region having the polypeptide sequence of SEQ ID NO:22;
l. a heavy chain variable region having the polypeptide sequence of SEQ ID NO:23, and a light chain variable region having the polypeptide sequence of SEQ ID NO:24;
m. a heavy chain variable region having the polypeptide sequence of SEQ ID NO:25, and a light chain variable region having the polypeptide sequence of SEQ ID NO:26;
n. a heavy chain variable region having the polypeptide sequence of SEQ ID NO:27, and a light chain variable region having the polypeptide sequence of SEQ ID NO:28;
o. a heavy chain variable region having the polypeptide sequence of SEQ ID NO:29, and a light chain variable region having the polypeptide sequence of SEQ ID NO:30;
p. a heavy chain variable region having the polypeptide sequence of SEQ ID NO:31, and a light chain variable region having the polypeptide sequence of SEQ ID NO:32;
q. a heavy chain variable region having the polypeptide sequence of SEQ ID NO:33, and a light chain variable region having the polypeptide sequence of SEQ ID NO:34;
r. a heavy chain variable region having the polypeptide sequence of SEQ ID NO:35, and a light chain variable region having the polypeptide sequence of SEQ ID NO:36;
s. a heavy chain variable region having the polypeptide sequence of SEQ ID NO:37, and a light chain variable region having the polypeptide sequence of SEQ ID NO:38;
t. a heavy chain variable region having the polypeptide sequence of SEQ ID NO:39, and a light chain variable region having the polypeptide sequence of SEQ ID NO:40;
u. a heavy chain variable region having the polypeptide sequence of SEQ ID NO:41, and a light chain variable region having the polypeptide sequence of SEQ ID NO:42;
v. a heavy chain variable region having the polypeptide sequence of SEQ ID NO:171, and a light chain variable region having the polypeptide sequence of SEQ ID NO:175;
w. a heavy chain variable region having the polypeptide sequence of SEQ ID NO:172, and a light chain variable region having the polypeptide sequence of SEQ ID NO:175;
x. a heavy chain variable region having the polypeptide sequence of SEQ ID NO:173, and a light chain variable region having the polypeptide sequence of SEQ ID NO:176; or y. a heavy chain variable region having the polypeptide sequence of SEQ ID NO:174, and a light chain variable region having the polypeptide sequence of SEQ ID NO:176.

4. The isolated monoclonal antibody or antigen-binding fragment of claim 1, wherein the antibody or antigen-binding fragment thereof is chimeric and/or humanized.

5. The isolated monoclonal antibody or antigen-binding fragment of claim 1, wherein the antibody or antigen-binding fragment thereof is capable of blocking binding of TIM-3 to phosphatidylserine (PtdSer).

6. An isolated nucleic acid encoding the monoclonal antibody or antigen-binding fragment of claim 1.

7. A vector comprising the isolated nucleic acid of claim 6.

8. A host cell comprising the vector of claim 7.

9. A pharmaceutical composition, comprising the isolated monoclonal antibody or antigen-binding fragment of claim 1 and a pharmaceutically acceptable carrier.

10. A method of blocking binding of TIM-3 to phosphatidylserine (PtdSer) in a subject in need thereof, comprising administering to the subject the pharmaceutical composition of claim 9.

11. A method of treating a disease or condition selected from the group consisting of a cancer and an infectious disease in a subject in need thereof, comprising administering to the subject the pharmaceutical composition of claim 9.

12. A method of producing the monoclonal antibody or antigen-binding fragment of claim 1, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or culture.

13. A method of producing a pharmaceutical composition comprising the monoclonal antibody or antigen-binding fragment of claim 1, comprising combining the monoclonal antibody or antigen-binding fragment with a pharmaceutically acceptable carrier to obtain the pharmaceutical composition.

14. A method of determining a level of TIM-3 in a subject, comprising (a) obtaining a sample from the subject; (b) contacting the sample with a monoclonal antibody or antigen-binding fragment thereof of claim 1; and (c) determining the level of TIM-3 in the subject.

15. The method of claim 14, wherein the sample is a tissue sample or blood sample.

16. The method of claim 15, wherein the tissue sample is a cancer tissue sample.

17. A bispecific antibody comprising the monoclonal antibody or antigen-binding fragment thereof of claim 1.

18. The monoclonal antibody or antigen-binding fragment thereof of claim 1, wherein the monoclonal antibody or antigen-binding fragment thereof specifically binds human TIM-3.

\* \* \* \* \*

SEQUENCE LISTING

<160> NUMBER OF SEQ ID NOS: 177

<210> SEQ ID NO 1
<211> LENGTH: 114
<212> TYPE: PRT
<213> ORGANISM: Artificial Sequence
<220> FEATURE:
<223> OTHER INFORMATION: 20-L10-A Heavy Chain Variable Region

<400> SEQUENCE: 1

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Val Leu Lys Trp Met
        35                  40                  45

Val Trp Ile Asn Thr Tyr Thr Gly Glu Pro Thr Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Ala Met Asp Tyr Trp Gly Gln Gly Thr Ser Val Thr Val
            100                 105                 110

Ser Ser
```

<210> SEQ ID NO 2
<211> LENGTH: 112
<212> TYPE: PRT
<213> ORGANISM: Artificial Sequence
<220> FEATURE:
<223> OTHER INFORMATION: 20-L10-A Light Chain Variable Region

<400> SEQUENCE: 2

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Trp Thr Phe Gly Gly Gly Thr Lys Leu Glu Ile Lys
            100                 105                 110
```

<210> SEQ ID NO 3
<211> LENGTH: 114
<212> TYPE: PRT
<213> ORGANISM: Artificial Sequence
<220> FEATURE:
<223> OTHER INFORMATION: 15-L23-A Heavy Chain Variable Region

<400> SEQUENCE: 3

```
Gln Ile Gln Leu Val Gln Ser Gly Pro Glu Leu Lys Lys Pro Gly Glu
1               5                   10                  15
```

```
Thr Val Lys Ile Ser Cys Arg Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Val Trp Ile Asn Thr Tyr Thr Gly Glu Pro Thr Phe Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Ile Asn Leu Lys Asn Glu Asp Thr Ala Thr Tyr Phe Cys
                85                  90                  95

Ala Arg Asp Thr Met Asp Tyr Trp Gly Gln Gly Thr Ser Val Thr Val
            100                 105                 110

Ser Ser

<210> SEQ ID NO 4
<211> LENGTH: 112
<212> TYPE: PRT
<213> ORGANISM: Artificial Sequence
<220> FEATURE:
<223> OTHER INFORMATION: 15-L23-A Light Chain Variable Region

<400> SEQUENCE: 4

Asp Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Trp Thr Phe Gly Gly Gly Thr Lys Leu Glu Ile Lys
            100                 105                 110

<210> SEQ ID NO 5
<211> LENGTH: 114
<212> TYPE: PRT
<213> ORGANISM: Artificial Sequence
<220> FEATURE:
<223> OTHER INFORMATION: 8-F3-A Heavy Chain Variable Region

<400> SEQUENCE: 5

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Ala Trp Ile Asn Thr Tyr Thr Gly Glu Pro Tyr Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95
```

```
Ala Arg Asp Leu Glu Asp Tyr Trp Gly Gln Gly Thr Thr Leu Thr Val
                100                 105                 110

Ser Ser

<210> SEQ ID NO 6
<211> LENGTH: 112
<212> TYPE: PRT
<213> ORGANISM: Artificial Sequence
<220> FEATURE:
<223> OTHER INFORMATION: 8-F3-A Light Chain Variable Region

<400> SEQUENCE: 6

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Trp Thr Phe Gly Gly Gly Thr Lys Leu Glu Ile Lys
                100                 105                 110

<210> SEQ ID NO 7
<211> LENGTH: 114
<212> TYPE: PRT
<213> ORGANISM: Artificial Sequence
<220> FEATURE:
<223> OTHER INFORMATION: 7-P15-A Heavy Chain Variable Region

<400> SEQUENCE: 7

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Leu Met Asp Tyr Trp Gly Gln Gly Thr Thr Leu Thr Val
                100                 105                 110

Ser Ser

<210> SEQ ID NO 8
<211> LENGTH: 112
<212> TYPE: PRT
<213> ORGANISM: Artificial Sequence
<220> FEATURE:
<223> OTHER INFORMATION: 7-P15-A Light Chain Variable Region

<400> SEQUENCE: 8
```

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Leu Gly Val Tyr Phe Cys Ser Gln Ser
            85                  90                  95

Ile His Val Pro Tyr Thr Phe Gly Gly Gly Thr Lys Leu Glu Ile Lys
            100                 105                 110
```

<210> SEQ ID NO 9
<211> LENGTH: 119
<212> TYPE: PRT
<213> ORGANISM: Artificial Sequence
<220> FEATURE:
<223> OTHER INFORMATION: 18-N1-A Heavy Chain Variable Region

<400> SEQUENCE: 9

```
Gln Val Gln Leu Gln Gln Pro Gly Ala Glu Leu Val Arg Pro Gly Val
1               5                   10                  15

Ser Val Lys Leu Ser Cys Lys Ala Ser Gly Tyr Thr Phe Thr Ser Tyr
            20                  25                  30

Trp Met His Trp Ile Lys Gln Arg Pro Glu Gln Gly Leu Glu Arg Ile
        35                  40                  45

Gly Glu Ile Asn Pro Ser Asn Gly Gly Thr Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Ser Tyr Tyr Thr Tyr Asp Ala Ile Asp Tyr Trp Gly Gln Gly
            100                 105                 110

Thr Ser Val Thr Val Ser Ser
        115
```

<210> SEQ ID NO 10
<211> LENGTH: 112
<212> TYPE: PRT
<213> ORGANISM: Artificial Sequence
<220> FEATURE:
<223> OTHER INFORMATION: 18-N1-A Light Chain Variable Region

<400> SEQUENCE: 10

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80
```

```
Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110
```

<210> SEQ ID NO 11
<211> LENGTH: 122
<212> TYPE: PRT
<213> ORGANISM: Artificial Sequence
<220> FEATURE:
<223> OTHER INFORMATION: 18-O22-A Heavy Chain Variable Region

<400> SEQUENCE: 11

```
Glu Val Gln Leu Gln Gln Ser Gly Pro Glu Leu Val Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Val Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Ser Ser Asp Tyr Asp Asp Gly His Trp Tyr Phe Asp Val Trp
            100                 105                 110

Gly Ala Gly Thr Thr Val Thr Val Ser Ser
            115                 120
```

<210> SEQ ID NO 12
<211> LENGTH: 112
<212> TYPE: PRT
<213> ORGANISM: Artificial Sequence
<220> FEATURE:
<223> OTHER INFORMATION: 18-O22-A Light Chain Variable Region

<400> SEQUENCE: 12

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Glu Ser Tyr Met Asn Trp Tyr Gln Gln Lys Pro Gly Gln Pro Pro
        35                  40                  45

Lys Leu Leu Ile Tyr Val Ala Ser Asn Leu Glu Ser Gly Ile Pro Val
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Thr Trp Thr Phe Gly Gly Gly Thr Lys Leu Glu Ile Lys
            100                 105                 110
```

<210> SEQ ID NO 13
<211> LENGTH: 116
<212> TYPE: PRT
<213> ORGANISM: Artificial Sequence
<220> FEATURE:
<223> OTHER INFORMATION: 16-L3-A Heavy Chain Variable Region

<400> SEQUENCE: 13

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
50                  55                  60

Lys Gly Lys Thr Thr Leu Thr Ala Asp Lys Ser Ser Thr Ala Tyr
65                  70                  75                  80

Met Leu Leu Ser Ser Leu Thr Ser Glu Asp Ser Ala Ile Tyr Phe Cys
            85                  90                  95

Ala Thr Asp Arg Tyr Asp Val Ala Tyr Trp Gly Gln Gly Thr Leu Val
            100                 105                 110

Thr Val Ser Ala
            115

<210> SEQ ID NO 14
<211> LENGTH: 108
<212> TYPE: PRT
<213> ORGANISM: Artificial Sequence
<220> FEATURE:
<223> OTHER INFORMATION: 16-L3-A Light Chain Variable Region

<400> SEQUENCE: 14

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Val Arg Phe Ser
50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
            85                  90                  95

Leu Thr Phe Gly Ala Gly Thr Lys Leu Glu Leu Lys
            100                 105

<210> SEQ ID NO 15
<211> LENGTH: 113
<212> TYPE: PRT
<213> ORGANISM: Artificial Sequence
<220> FEATURE:
<223> OTHER INFORMATION: 16-K5-A Heavy Chain Variable Region

<400> SEQUENCE: 15

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Ser
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
50                  55                  60

```
Lys Gly Lys Ala Thr Leu Thr Thr Asp Lys Ser Ser Thr Ala Tyr
 65                  70                  75                  80

Met Gln Leu Ser Arg Leu Thr Ser Glu Asp Ser Ala Val Tyr Phe Cys
                 85                  90                  95

Ala Arg Gly Leu Asp Tyr Trp Gly Gln Gly Thr Thr Leu Thr Val Ser
            100                 105                 110

Ser
```

```
<210> SEQ ID NO 16
<211> LENGTH: 107
<212> TYPE: PRT
<213> ORGANISM: Artificial Sequence
<220> FEATURE:
<223> OTHER INFORMATION: 16-K5-A Light Chain Variable Region

<400> SEQUENCE: 16

Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
                 20                  25                  30

Leu Gly Trp Phe Gln Gln Lys Pro Gly Lys Ser Pro Lys Thr Leu Ile
             35                  40                  45

Tyr Arg Ala Asp Arg Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Glu Phe Pro Leu
                 85                  90                  95

Thr Phe Gly Ala Gly Thr Lys Leu Glu Leu Lys
            100                 105
```

```
<210> SEQ ID NO 17
<211> LENGTH: 120
<212> TYPE: PRT
<213> ORGANISM: Artificial Sequence
<220> FEATURE:
<223> OTHER INFORMATION: 19-A14-A Heavy Chain Variable Region

<400> SEQUENCE: 17

Asp Val Gln Leu Gln Gly Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
                 20                  25                  30

Tyr Ala Trp Asn Trp Ile Arg Gln Phe Pro Gly Asn Ile Leu Glu Trp
             35                  40                  45

Met Gly Tyr Ile Ser Tyr Ser Gly Ser Thr Ser Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Arg Asp Gly Arg Tyr Asp Tyr Tyr Ala Met Asp Tyr Trp Gly Gln
            100                 105                 110

Gly Thr Ser Val Thr Val Ser Ser
            115                 120
```

```
<210> SEQ ID NO 18
```

<211> LENGTH: 111
<212> TYPE: PRT
<213> ORGANISM: Artificial Sequence
<220> FEATURE:
<223> OTHER INFORMATION: 19-A14-A Light Chain Variable Region

<400> SEQUENCE: 18

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Phe Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys His Gln Ser Lys
                85                  90                  95

Glu Val Pro Trp Thr Phe Gly Gly Gly Thr Lys Leu Glu Ile Lys
            100                 105                 110
```

<210> SEQ ID NO 19
<211> LENGTH: 117
<212> TYPE: PRT
<213> ORGANISM: Artificial Sequence
<220> FEATURE:
<223> OTHER INFORMATION: 2-K2-A Heavy Chain Variable Region

<400> SEQUENCE: 19

```
Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ser Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Asn Asp His Glu Gly Gly Phe Ala Tyr Trp Gly Gln Gly Thr Leu
            100                 105                 110

Val Thr Val Ser Ala
        115
```

<210> SEQ ID NO 20
<211> LENGTH: 107
<212> TYPE: PRT
<213> ORGANISM: Artificial Sequence
<220> FEATURE:
<223> OTHER INFORMATION: 2-K2-A Light Chain Variable Region

<400> SEQUENCE: 20

```
Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30
```

Ile Gly Trp Leu Gln Gln Lys Pro Gly Lys Ser Phe Lys Gly Leu Ile
         35                  40                  45

Tyr His Gly Thr Asn Leu Glu Asp Gly Val Pro Ser Arg Phe Ser Gly
     50                  55                  60

Ser Gly Ser Gly Ala Asp Tyr Ser Leu Thr Ile Ser Ser Leu Glu Ser
 65                  70                  75                  80

Glu Asp Phe Ala Asp Tyr Tyr Cys Val Gln Tyr Ala Gln Phe Pro Phe
                 85                  90                  95

Thr Phe Gly Ser Gly Thr Lys Leu Glu Ile Lys
            100                 105

<210> SEQ ID NO 21
<211> LENGTH: 123
<212> TYPE: PRT
<213> ORGANISM: Artificial Sequence
<220> FEATURE:
<223> OTHER INFORMATION: 6-H6-A Heavy Chain Variable Region

<400> SEQUENCE: 21

Glu Val Gln Leu Gln Gln Phe Gly Ala Glu Leu Val Lys Pro Gly Ala
1                5                  10                  15

Ser Val Lys Ile Ser Cys Lys Ala Ser Gly Tyr Thr Phe Thr Asp Tyr
             20                  25                  30

Asn Met Asp Trp Val Lys Gln Ser His Gly Lys Ser Leu Glu Trp Ile
         35                  40                  45

Gly Asp Ile Asp Pro Asn Tyr Asp Ser Thr Thr Tyr Asn Gln Lys Phe
     50                  55                  60

Lys Gly Lys Ala Thr Leu Thr Val Asp Lys Ser Ser Thr Ala Tyr
 65                  70                  75                  80

Met Glu Leu Arg Ser Leu Thr Ser Glu Asp Thr Ala Val Tyr Tyr Cys
                 85                  90                  95

Ala Arg Gly Gly His Tyr Arg Tyr Asp Gly Tyr Ala Met Asp Tyr
            100                 105                 110

Trp Gly Gln Gly Thr Ser Val Thr Val Ser Ser
        115                 120

<210> SEQ ID NO 22
<211> LENGTH: 111
<212> TYPE: PRT
<213> ORGANISM: Artificial Sequence
<220> FEATURE:
<223> OTHER INFORMATION: 6-H6-A Light Chain Variable Region

<400> SEQUENCE: 22

Asp Ile Val Leu Thr Gln Ser Pro Ala Ser Ser Ala Val Ser Leu Gly
1                5                  10                  15

Gln Arg Ala Thr Phe Ser Cys Arg Ala Ser Gln Ser Val Ser Thr Ser
             20                  25                  30

Ser Tyr Ser Phe Met His Trp Tyr Gln Gln Lys Pro Gly Gln Pro Pro
         35                  40                  45

Lys Leu Leu Ile Lys Tyr Ala Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Thr Ala Thr Tyr Tyr Cys Gln His Ser Trp
                 85                  90                  95

Glu Ile Pro Pro Thr Phe Gly Gly Gly Thr Asn Leu Glu Ile Lys
            100                 105                 110

<210> SEQ ID NO 23
<211> LENGTH: 123
<212> TYPE: PRT
<213> ORGANISM: Artificial Sequence
<220> FEATURE:
<223> OTHER INFORMATION: 1-A19-A Heavy Chain Variable Region

<400> SEQUENCE: 23

Glu Val Gln Leu Gln Gln Phe Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asp Pro Asn Tyr Asp Ile Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Gly His Tyr Arg Tyr Asp Gly Tyr Tyr Ala Leu Asp Tyr
            100                 105                 110

Trp Gly Gln Gly Thr Ser Val Thr Val Ser Ser
        115                 120

<210> SEQ ID NO 24
<211> LENGTH: 111
<212> TYPE: PRT
<213> ORGANISM: Artificial Sequence
<220> FEATURE:
<223> OTHER INFORMATION: 1-A19-A Light Chain Variable Region

<400> SEQUENCE: 24

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Ser Gly Thr Lys Leu Glu Ile Lys
            100                 105                 110

<210> SEQ ID NO 25
<211> LENGTH: 120
<212> TYPE: PRT
<213> ORGANISM: Artificial Sequence
<220> FEATURE:
<223> OTHER INFORMATION: 10-O15-A Heavy Chain Variable Region

<400> SEQUENCE: 25

Gln Val Gln Leu Gln Gln Ser Gly Ala Asp Leu Val Arg Pro Gly Ala
1               5                   10                  15

-continued

```
Ser Val Lys Leu Ser Cys Lys Ala Leu Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile His Pro Gly Ser Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Ser Ser Leu Thr Ser Glu Asp Ser Ala Val Tyr Phe Cys
                85                  90                  95

Ser Arg Ser Tyr Tyr Arg Tyr Thr Gly Tyr Phe Asp Val Trp Gly Ala
            100                 105                 110

Gly Thr Thr Val Thr Val Ser Ser
        115                 120
```

<210> SEQ ID NO 26
<211> LENGTH: 111
<212> TYPE: PRT
<213> ORGANISM: Artificial Sequence
<220> FEATURE:
<223> OTHER INFORMATION: 10-O15-A Light Chain Variable Region

<400> SEQUENCE: 26

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ala Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Val His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys
            100                 105                 110
```

<210> SEQ ID NO 27
<211> LENGTH: 122
<212> TYPE: PRT
<213> ORGANISM: Artificial Sequence
<220> FEATURE:
<223> OTHER INFORMATION: 6-I13-A Heavy Chain Variable Region

<400> SEQUENCE: 27

```
Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Val Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95
```

```
Ala Ser Tyr Ser Leu Thr Tyr Asp Gly Tyr Tyr Pro Phe Ala Tyr Trp
            100                 105                 110

Gly Gln Gly Thr Leu Val Thr Val Ser Ala
        115                 120

<210> SEQ ID NO 28
<211> LENGTH: 111
<212> TYPE: PRT
<213> ORGANISM: Artificial Sequence
<220> FEATURE:
<223> OTHER INFORMATION: 6-I13-A Light Chain Variable Region

<400> SEQUENCE: 28

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys
            100                 105                 110

<210> SEQ ID NO 29
<211> LENGTH: 120
<212> TYPE: PRT
<213> ORGANISM: Artificial Sequence
<220> FEATURE:
<223> OTHER INFORMATION: 5-K4-A Heavy Chain Variable Region

<400> SEQUENCE: 29

Glu Val Gln Leu Gln Gln Ser Gly Pro Glu Leu Val Lys Thr Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ser His Gly Lys Ser Leu Glu Trp Ile
        35                  40                  45

Gly His Ile Ser Cys Phe Asn Gly Ala Thr Ser Tyr Asn Gln Lys Phe
    50                  55                  60

Lys Gly Lys Ala Thr Phe Thr Val Asp Thr Ser Ser Ser Thr Ala Tyr
65                  70                  75                  80

Met Gln Phe Asn Ser Leu Thr Ser Glu Asp Ser Ala Val Tyr Tyr Cys
                85                  90                  95

Ala Arg Arg Gly Asp Phe Asp Arg Pro Glu Phe Ala Tyr Trp Gly Gln
            100                 105                 110

Gly Thr Leu Val Thr Val Ser Ala
        115                 120

<210> SEQ ID NO 30
<211> LENGTH: 111
<212> TYPE: PRT
<213> ORGANISM: Artificial Sequence
<220> FEATURE:
<223> OTHER INFORMATION: 5-K4-A Light Chain Variable Region
```

```
<400> SEQUENCE: 30

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Trp Thr Phe Gly Gly Gly Thr Lys Leu Glu Ile Lys
            100                 105                 110

<210> SEQ ID NO 31
<211> LENGTH: 120
<212> TYPE: PRT
<213> ORGANISM: Artificial Sequence
<220> FEATURE:
<223> OTHER INFORMATION: 12-G18-A Heavy Chain Variable Region

<400> SEQUENCE: 31

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Gly Asp Thr Ala Thr Tyr Tyr Cys
                85                  90                  95

Ala Ser Asn Tyr Arg Tyr Asp Tyr Trp Phe Phe Gly Val Trp Gly Ala
            100                 105                 110

Gly Thr Thr Val Thr Val Ser Ser
            115                 120

<210> SEQ ID NO 32
<211> LENGTH: 111
<212> TYPE: PRT
<213> ORGANISM: Artificial Sequence
<220> FEATURE:
<223> OTHER INFORMATION: 12-G18-A Light Chain Variable Region

<400> SEQUENCE: 32

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Glu Ser Asn Gln Gly Ser Gly Val Pro Ala
    50                  55                  60
```

Arg Phe Ser Gly Ser Gly Ser Gly Thr Asp Phe Ser Leu Asn Ile His
 65                  70                  75                  80

Pro Met Glu Glu Asp Asp Thr Ala Met Tyr Phe Cys Gln Gln Ser Lys
                 85                  90                  95

Glu Val Pro Tyr Thr Phe Gly Gly Gly Thr Lys Leu Glu Ile Lys
            100                 105                 110

<210> SEQ ID NO 33
<211> LENGTH: 114
<212> TYPE: PRT
<213> ORGANISM: Artificial Sequence
<220> FEATURE:
<223> OTHER INFORMATION: 10-M21-A Heavy Chain Variable Region

<400> SEQUENCE: 33

Asp Val Gln Leu Gln Glu Ser Gly Pro Thr Leu Val Lys Pro Ser Gln
1               5                   10                  15

Thr Leu Ser Leu Thr Cys Ser Val Thr Gly Asp Ser Ile Thr Ser Gly
                20                  25                  30

Tyr Trp Asn Trp Ile Arg Lys Phe Pro Gly Asn Lys Leu Glu Tyr Met
            35                  40                  45

Gly Tyr Ile Ser Tyr Ser Gly Ser Thr Tyr Tyr Asn Pro Ser Leu Lys
        50                  55                  60

Ser Arg Ile Ser Ile Ile Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Val
                85                  90                  95

Ser Gly Asn His Phe Asp Tyr Trp Gly Gln Gly Thr Thr Leu Thr Val
            100                 105                 110

Ser Ser

<210> SEQ ID NO 34
<211> LENGTH: 107
<212> TYPE: PRT
<213> ORGANISM: Artificial Sequence
<220> FEATURE:
<223> OTHER INFORMATION: 10-M21-A Light Chain Variable Region

<400> SEQUENCE: 34

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Arg Tyr
                20                  25                  30

Ile Ala Trp Tyr Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Phe
                85                  90                  95

Thr Phe Gly Ser Gly Thr Lys Leu Glu Ile Lys
            100                 105

<210> SEQ ID NO 35
<211> LENGTH: 122
<212> TYPE: PRT
<213> ORGANISM: Artificial Sequence

```
<220> FEATURE:
<223> OTHER INFORMATION: 12-M11-A Heavy Chain Variable Region

<400> SEQUENCE: 35

Ser Gln Val Gln Leu Gln Gln Ser Gly Ala Glu Leu Ala Lys Pro Gly
1               5                   10                  15

Ala Ser Val Lys Met Ser Cys Lys Ala Ser Gly Tyr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ile Thr Gly Tyr Thr Glu Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Arg Leu Thr Ser Glu Asp Ser Ala Val Tyr Tyr Cys
                85                  90                  95

Ala Arg Gly Val Glu Asn Phe Asp Tyr Leu Tyr Ala Met Asp Tyr Trp
            100                 105                 110

Gly Gln Gly Ala Ser Val Thr Val Ser Ser
        115                 120

<210> SEQ ID NO 36
<211> LENGTH: 105
<212> TYPE: PRT
<213> ORGANISM: Artificial Sequence
<220> FEATURE:
<223> OTHER INFORMATION: 12-M11-A Light Chain Variable Region

<400> SEQUENCE: 36

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Thr Arg Phe Asn Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Arg Thr Phe
                85                  90                  95

Gly Gly Gly Thr Lys Leu Glu Ile Lys
            100                 105

<210> SEQ ID NO 37
<211> LENGTH: 121
<212> TYPE: PRT
<213> ORGANISM: Artificial Sequence
<220> FEATURE:
<223> OTHER INFORMATION: 5-C11-A Heavy Chain Variable Region

<400> SEQUENCE: 37

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Phe
            20                  25                  30

Tyr Met Tyr Trp Val Arg Gln Thr Pro Glu Lys Arg Leu Glu Trp Val
        35                  40                  45
```

Ala Thr Ile Ser Asp Gly Gly Ser Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Ser Gly Tyr Tyr Tyr Gly Ser Asp Tyr Val Met Asp Tyr Trp Gly
                100                 105                 110

Gln Gly Thr Ser Val Thr Val Ser Ser
            115                 120

<210> SEQ ID NO 38
<211> LENGTH: 112
<212> TYPE: PRT
<213> ORGANISM: Artificial Sequence
<220> FEATURE:
<223> OTHER INFORMATION: 5-C11-A Light Chain Variable Region

<400> SEQUENCE: 38

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Asp Asp Leu Ala Val Tyr Tyr Cys Lys Gln
                85                  90                  95

Ser Tyr Asn Leu Leu Thr Phe Gly Ala Gly Thr Lys Leu Glu Leu Lys
                100                 105                 110

<210> SEQ ID NO 39
<211> LENGTH: 118
<212> TYPE: PRT
<213> ORGANISM: Artificial Sequence
<220> FEATURE:
<223> OTHER INFORMATION: 16-J5-A Heavy Chain Variable Region

<400> SEQUENCE: 39

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met Asn Trp Val Arg Gln Ala Pro Glu Lys Gly Leu Glu Trp Val
            35                  40                  45

Ala Tyr Ile Ser Ser Gly Ser Ser Thr Ile Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Trp Gly Arg Trp Ala Asp Phe Asp Tyr Trp Gly Gln Gly Thr
                100                 105                 110

Thr Leu Thr Val Ser Ser
            115

```
<210> SEQ ID NO 40
<211> LENGTH: 111
<212> TYPE: PRT
<213> ORGANISM: Artificial Sequence
<220> FEATURE:
<223> OTHER INFORMATION: 16-J5-A Light Chain Variable Region

<400> SEQUENCE: 40
```

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Pro Thr Phe Gly Gly Gly Thr Lys Leu Glu Ile Lys
            100                 105                 110

```
<210> SEQ ID NO 41
<211> LENGTH: 120
<212> TYPE: PRT
<213> ORGANISM: Artificial Sequence
<220> FEATURE:
<223> OTHER INFORMATION: 7-N2-A Heavy Chain Variable Region

<400> SEQUENCE: 41
```

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Phe
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Thr Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp Tyr Tyr Gly Tyr Val Gly Asn Ala Met Asp Tyr Trp Gly Gln
            100                 105                 110

Gly Thr Ser Val Thr Val Ser Ser
        115                 120

```
<210> SEQ ID NO 42
<211> LENGTH: 113
<212> TYPE: PRT
<213> ORGANISM: Artificial Sequence
<220> FEATURE:
<223> OTHER INFORMATION: 7-N2-A Light Chain Variable Region

<400> SEQUENCE: 42
```

Asp Ile Val Met Ser Gln Ser Pro Ser Ser Leu Ala Val Ser Ala Gly
1               5                   10                  15

-continued

```
Glu Lys Val Thr Met Ser Cys Lys Ser Ser Gln Ser Leu Leu Asn Ser
             20                  25                  30

Arg Thr Arg Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn His Met Tyr Thr Phe Gly Gly Gly Thr Lys Leu Glu Ile
            100                 105                 110

Lys

<210> SEQ ID NO 43
<211> LENGTH: 8
<212> TYPE: PRT
<213> ORGANISM: Artificial Sequence
<220> FEATURE:
<223> OTHER INFORMATION: 20-L10-A HC CDR1

<400> SEQUENCE: 43

Gly Tyr Thr Phe Thr Asn Tyr Gly
1               5

<210> SEQ ID NO 44
<211> LENGTH: 8
<212> TYPE: PRT
<213> ORGANISM: Artificial Sequence
<220> FEATURE:
<223> OTHER INFORMATION: 20-L10-A HC CDR2

<400> SEQUENCE: 44

Ile Asn Thr Tyr Thr Gly Glu Pro
1               5

<210> SEQ ID NO 45
<211> LENGTH: 7
<212> TYPE: PRT
<213> ORGANISM: Artificial Sequence
<220> FEATURE:
<223> OTHER INFORMATION: 20-L10-A HC CDR3

<400> SEQUENCE: 45

Ala Arg Asp Ala Met Asp Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: 15-L23-A HC CDR1

<400> SEQUENCE: 46

Gly Tyr Thr Phe Thr Asn Tyr Gly
1               5

<210> SEQ ID NO 47
<211> LENGTH: 8
<212> TYPE: PRT
<213> ORGANISM: Artificial Sequence
<220> FEATURE:
<223> OTHER INFORMATION: 15-L23-A HC CDR2
```

```
<400> SEQUENCE: 47

Ile Asn Thr Tyr Thr Gly Glu Pro
1               5

<210> SEQ ID NO 48
<211> LENGTH: 7
<212> TYPE: PRT
<213> ORGANISM: Artificial Sequence
<220> FEATURE:
<223> OTHER INFORMATION: 15-L23-A HC CDR3

<400> SEQUENCE: 48

Ala Arg Asp Thr Met Asp Tyr
1               5

<210> SEQ ID NO 49
<211> LENGTH: 8
<212> TYPE: PRT
<213> ORGANISM: Artificial Sequence
<220> FEATURE:
<223> OTHER INFORMATION: 8-F3-A HC CDR1

<400> SEQUENCE: 49

Gly Tyr Thr Phe Thr Asn Tyr Gly
1               5

<210> SEQ ID NO 50
<211> LENGTH: 8
<212> TYPE: PRT
<213> ORGANISM: Artificial Sequence
<220> FEATURE:
<223> OTHER INFORMATION: 8-F3-A HC CDR2

<400> SEQUENCE: 50

Ile Asn Thr Tyr Thr Gly Glu Pro
1               5

<210> SEQ ID NO 51
<211> LENGTH: 7
<212> TYPE: PRT
<213> ORGANISM: Artificial Sequence
<220> FEATURE:
<223> OTHER INFORMATION: 8-F3-A HC CDR3

<400> SEQUENCE: 51

Ala Arg Asp Leu Glu Asp Tyr
1               5

<210> SEQ ID NO 52
<211> LENGTH: 8
<212> TYPE: PRT
<213> ORGANISM: Artificial Sequence
<220> FEATURE:
<223> OTHER INFORMATION: 7-P15-A CDR1

<400> SEQUENCE: 52

Gly Tyr Thr Phe Thr Asn Tyr Gly
1               5

<210> SEQ ID NO 53
<211> LENGTH: 8
<212> TYPE: PRT
<213> ORGANISM: Artificial Sequence
<220> FEATURE:
<223> OTHER INFORMATION: 7-P15-A CDR2
```

```
<400> SEQUENCE: 53

Ile Asn Thr Tyr Thr Gly Glu Pro
1               5

<210> SEQ ID NO 54
<211> LENGTH: 7
<212> TYPE: PRT
<213> ORGANISM: Artificial Sequence
<220> FEATURE:
<223> OTHER INFORMATION: 7-P15-A CDR3

<400> SEQUENCE: 54

Ala Arg Asp Leu Met Asp Tyr
1               5

<210> SEQ ID NO 55
<211> LENGTH: 8
<212> TYPE: PRT
<213> ORGANISM: Artificial Sequence
<220> FEATURE:
<223> OTHER INFORMATION: 18-N1-A HC CDR1

<400> SEQUENCE: 55

Gly Tyr Thr Phe Thr Ser Tyr Trp
1               5

<210> SEQ ID NO 56
<211> LENGTH: 8
<212> TYPE: PRT
<213> ORGANISM: Artificial Sequence
<220> FEATURE:
<223> OTHER INFORMATION: 18-N1-A HC CDR2

<400> SEQUENCE: 56

Ile Asn Pro Ser Asn Gly Gly Thr
1               5

<210> SEQ ID NO 57
<211> LENGTH: 12
<212> TYPE: PRT
<213> ORGANISM: Artificial Sequence
<220> FEATURE:
<223> OTHER INFORMATION: 18-N1-A HC CDR3

<400> SEQUENCE: 57

Ala Arg Ser Tyr Tyr Thr Tyr Asp Ala Ile Asp Tyr
1               5                   10

<210> SEQ ID NO 58
<211> LENGTH: 8
<212> TYPE: PRT
<213> ORGANISM: Artificial Sequence
<220> FEATURE:
<223> OTHER INFORMATION: 18-O22-A HC CDR1

<400> SEQUENCE: 58

Gly Tyr Thr Phe Thr Ser Tyr Val
1               5

<210> SEQ ID NO 59
<211> LENGTH: 8
<212> TYPE: PRT
<213> ORGANISM: Artificial Sequence
<220> FEATURE:
<223> OTHER INFORMATION: 18-O22-A HC CDR2

<400> SEQUENCE: 59
```

```
Ile Asn Pro Tyr Asn Asp Val Thr
1               5
```

<210> SEQ ID NO 60
<211> LENGTH: 15
<212> TYPE: PRT
<213> ORGANISM: Artificial Sequence
<220> FEATURE:
<223> OTHER INFORMATION: 18-O22-A HC CDR3

<400> SEQUENCE: 60

```
Ala Arg Ser Ser Asp Tyr Asp Asp Gly His Trp Tyr Phe Asp Val
1               5                   10                  15
```

<210> SEQ ID NO 61
<211> LENGTH: 8
<212> TYPE: PRT
<213> ORGANISM: Artificial Sequence
<220> FEATURE:
<223> OTHER INFORMATION: 16-L3-A HC CDR1

<400> SEQUENCE: 61

```
Gly Tyr Thr Phe Thr Ser Tyr Tyr
1               5
```

<210> SEQ ID NO 62
<211> LENGTH: 8
<212> TYPE: PRT
<213> ORGANISM: Artificial Sequence
<220> FEATURE:
<223> OTHER INFORMATION: 16-L3-A HC CDR2

<400> SEQUENCE: 62

```
Ile Tyr Pro Gly Asp Gly Ser Thr
1               5
```

<210> SEQ ID NO 63
<211> LENGTH: 9
<212> TYPE: PRT
<213> ORGANISM: Artificial Sequence
<220> FEATURE:
<223> OTHER INFORMATION: 16-L3-A HC CDR3

<400> SEQUENCE: 63

```
Ala Thr Asp Arg Tyr Asp Val Ala Tyr
1               5
```

<210> SEQ ID NO 64
<211> LENGTH: 8
<212> TYPE: PRT
<213> ORGANISM: Artificial Sequence
<220> FEATURE:
<223> OTHER INFORMATION: 16-K5-A HC CDR1

<400> SEQUENCE: 64

```
Gly Tyr Thr Phe Thr Ser Ser Asp
1               5
```

<210> SEQ ID NO 65
<211> LENGTH: 8
<212> TYPE: PRT
<213> ORGANISM: Artificial Sequence
<220> FEATURE:
<223> OTHER INFORMATION: 16-K5-A HC CDR2

<400> SEQUENCE: 65

```
Ile Phe Pro Gly Asp Gly Ser Thr
1               5

<210> SEQ ID NO 66
<211> LENGTH: 6
<212> TYPE: PRT
<213> ORGANISM: Artificial Sequence
<220> FEATURE:
<223> OTHER INFORMATION: 16-K5-A HC CDR3

<400> SEQUENCE: 66

Ala Arg Gly Leu Asp Tyr
1               5

<210> SEQ ID NO 67
<211> LENGTH: 9
<212> TYPE: PRT
<213> ORGANISM: Artificial Sequence
<220> FEATURE:
<223> OTHER INFORMATION: 19-A14-A HC CDR1

<400> SEQUENCE: 67

Gly Tyr Ser Ile Thr Ser Asp Tyr Ala
1               5

<210> SEQ ID NO 68
<211> LENGTH: 7
<212> TYPE: PRT
<213> ORGANISM: Artificial Sequence
<220> FEATURE:
<223> OTHER INFORMATION: 19-A14-A HC CDR2

<400> SEQUENCE: 68

Ile Ser Tyr Ser Gly Ser Thr
1               5

<210> SEQ ID NO 69
<211> LENGTH: 13
<212> TYPE: PRT
<213> ORGANISM: Artificial Sequence
<220> FEATURE:
<223> OTHER INFORMATION: 19-A14-A HC CDR3

<400> SEQUENCE: 69

Ala Arg Asp Gly Arg Tyr Asp Tyr Tyr Ala Met Asp Tyr
1               5                   10

<210> SEQ ID NO 70
<211> LENGTH: 8
<212> TYPE: PRT
<213> ORGANISM: Artificial Sequence
<220> FEATURE:
<223> OTHER INFORMATION: 2-K2-A HC CDR1

<400> SEQUENCE: 70

Gly Tyr Thr Phe Thr Thr Tyr Trp
1               5

<210> SEQ ID NO 71
<211> LENGTH: 8
<212> TYPE: PRT
<213> ORGANISM: Artificial Sequence
<220> FEATURE:
<223> OTHER INFORMATION: 2-K2-A HC CDR2

<400> SEQUENCE: 71

Ile Asn Pro Ser Thr Gly Tyr Thr
```

```
1               5

<210> SEQ ID NO 72
<211> LENGTH: 10
<212> TYPE: PRT
<213> ORGANISM: Artificial Sequence
<220> FEATURE:
<223> OTHER INFORMATION: 2-K2-A HC CDR3

<400> SEQUENCE: 72

Ala Asn Asp His Glu Gly Gly Phe Ala Tyr
1               5                   10

<210> SEQ ID NO 73
<211> LENGTH: 8
<212> TYPE: PRT
<213> ORGANISM: Artificial Sequence
<220> FEATURE:
<223> OTHER INFORMATION: 6-H6-A HC CDR1

<400> SEQUENCE: 73

Gly Tyr Thr Phe Thr Asp Tyr Asn
1               5

<210> SEQ ID NO 74
<211> LENGTH: 8
<212> TYPE: PRT
<213> ORGANISM: Artificial Sequence
<220> FEATURE:
<223> OTHER INFORMATION: 6-H6-A HC CDR2

<400> SEQUENCE: 74

Ile Asp Pro Asn Tyr Asp Ser Thr
1               5

<210> SEQ ID NO 75
<211> LENGTH: 16
<212> TYPE: PRT
<213> ORGANISM: Artificial Sequence
<220> FEATURE:
<223> OTHER INFORMATION: 6-H6-A HC CDR3

<400> SEQUENCE: 75

Ala Arg Gly Gly His Tyr Arg Tyr Asp Gly Tyr Tyr Ala Met Asp Tyr
1               5                   10                  15

<210> SEQ ID NO 76
<211> LENGTH: 8
<212> TYPE: PRT
<213> ORGANISM: Artificial Sequence
<220> FEATURE:
<223> OTHER INFORMATION: 1-A19-A HC CDR1

<400> SEQUENCE: 76

Gly Tyr Thr Phe Thr Asp Tyr Asn
1               5

<210> SEQ ID NO 77
<211> LENGTH: 8
<212> TYPE: PRT
<213> ORGANISM: Artificial Sequence
<220> FEATURE:
<223> OTHER INFORMATION: 1-A19-A HC CDR2

<400> SEQUENCE: 77

Ile Asp Pro Asn Tyr Asp Ile Thr
1               5
```

```
<210> SEQ ID NO 78
<211> LENGTH: 16
<212> TYPE: PRT
<213> ORGANISM: Artificial Sequence
<220> FEATURE:
<223> OTHER INFORMATION: 1-A19-A HC CDR3

<400> SEQUENCE: 78

Ala Arg Gly Gly His Tyr Arg Tyr Asp Gly Tyr Tyr Ala Leu Asp Tyr
1               5                   10                  15

<210> SEQ ID NO 79
<211> LENGTH: 8
<212> TYPE: PRT
<213> ORGANISM: Artificial Sequence
<220> FEATURE:
<223> OTHER INFORMATION: 10-O15-A HC CDR1

<400> SEQUENCE: 79

Gly Tyr Thr Phe Thr Asp Tyr Glu
1               5

<210> SEQ ID NO 80
<211> LENGTH: 8
<212> TYPE: PRT
<213> ORGANISM: Artificial Sequence
<220> FEATURE:
<223> OTHER INFORMATION: 10-O15-A HC CDR2

<400> SEQUENCE: 80

Ile His Pro Gly Ser Gly Gly Thr
1               5

<210> SEQ ID NO 81
<211> LENGTH: 13
<212> TYPE: PRT
<213> ORGANISM: Artificial Sequence
<220> FEATURE:
<223> OTHER INFORMATION: 10-O15-A HC CDR3

<400> SEQUENCE: 81

Ser Arg Ser Tyr Tyr Arg Tyr Thr Gly Tyr Phe Asp Val
1               5                   10

<210> SEQ ID NO 82
<211> LENGTH: 8
<212> TYPE: PRT
<213> ORGANISM: Artificial Sequence
<220> FEATURE:
<223> OTHER INFORMATION: 6-I13-A HC CDR1

<400> SEQUENCE: 82

Gly Tyr Ser Phe Thr Gly Tyr Asn
1               5

<210> SEQ ID NO 83
<211> LENGTH: 8
<212> TYPE: PRT
<213> ORGANISM: Artificial Sequence
<220> FEATURE:
<223> OTHER INFORMATION: 6-I13-A HC CDR2

<400> SEQUENCE: 83

Ile Asp Pro Tyr Tyr Gly Val Thr
1               5
```

<210> SEQ ID NO 84
<211> LENGTH: 15
<212> TYPE: PRT
<213> ORGANISM: Artificial Sequence
<220> FEATURE:
<223> OTHER INFORMATION: 6-I13-A HC CDR3

<400> SEQUENCE: 84

Ala Ser Tyr Ser Leu Thr Tyr Asp Gly Tyr Tyr Pro Phe Ala Tyr
1               5                   10                  15

<210> SEQ ID NO 85
<211> LENGTH: 8
<212> TYPE: PRT
<213> ORGANISM: Artificial Sequence
<220> FEATURE:
<223> OTHER INFORMATION: 5-K4-A HC CDR1

<400> SEQUENCE: 85

Gly Tyr Ser Phe Thr Ala Tyr Tyr
1               5

<210> SEQ ID NO 86
<211> LENGTH: 8
<212> TYPE: PRT
<213> ORGANISM: Artificial Sequence
<220> FEATURE:
<223> OTHER INFORMATION: 5-K4-A HC CDR2

<400> SEQUENCE: 86

Ile Ser Cys Phe Asn Gly Ala Thr
1               5

<210> SEQ ID NO 87
<211> LENGTH: 13
<212> TYPE: PRT
<213> ORGANISM: Artificial Sequence
<220> FEATURE:
<223> OTHER INFORMATION: 5-K4-A HC CDR3

<400> SEQUENCE: 87

Ala Arg Arg Gly Asp Phe Asp Arg Pro Glu Phe Ala Tyr
1               5                   10

<210> SEQ ID NO 88
<211> LENGTH: 9
<212> TYPE: PRT
<213> ORGANISM: Artificial Sequence
<220> FEATURE:
<223> OTHER INFORMATION: 12-G18-A HC CDR1

<400> SEQUENCE: 88

Gly Tyr Ser Ile Thr Ser Asp Tyr Ala
1               5

<210> SEQ ID NO 89
<211> LENGTH: 7
<212> TYPE: PRT
<213> ORGANISM: Artificial Sequence
<220> FEATURE:
<223> OTHER INFORMATION: 12-G18-A HC CDR2

<400> SEQUENCE: 89

Ile Ser Tyr Ser Gly Ser Thr
1               5

```
<210> SEQ ID NO 90
<211> LENGTH: 13
<212> TYPE: PRT
<213> ORGANISM: Artificial Sequence
<220> FEATURE:
<223> OTHER INFORMATION: 12-G18-A HC CDR3

<400> SEQUENCE: 90

Ala Ser Asn Tyr Arg Tyr Asp Tyr Trp Phe Phe Gly Val
1               5                   10

<210> SEQ ID NO 91
<211> LENGTH: 8
<212> TYPE: PRT
<213> ORGANISM: Artificial Sequence
<220> FEATURE:
<223> OTHER INFORMATION: 10-M21-A HC CDR1

<400> SEQUENCE: 91

Gly Asp Ser Ile Thr Ser Gly Tyr
1               5

<210> SEQ ID NO 92
<211> LENGTH: 7
<212> TYPE: PRT
<213> ORGANISM: Artificial Sequence
<220> FEATURE:
<223> OTHER INFORMATION: 10-M21-A HC CDR2

<400> SEQUENCE: 92

Ile Ser Tyr Ser Gly Ser Thr
1               5

<210> SEQ ID NO 93
<211> LENGTH: 8
<212> TYPE: PRT
<213> ORGANISM: Artificial Sequence
<220> FEATURE:
<223> OTHER INFORMATION: 10-M21-A HC CDR3

<400> SEQUENCE: 93

Val Ser Gly Asn His Phe Asp Tyr
1               5

<210> SEQ ID NO 94
<211> LENGTH: 7
<212> TYPE: PRT
<213> ORGANISM: Artificial Sequence
<220> FEATURE:
<223> OTHER INFORMATION: 12-M11-A HC CDR1

<400> SEQUENCE: 94

Gly Tyr Phe Thr Ser Tyr Trp
1               5

<210> SEQ ID NO 95
<211> LENGTH: 8
<212> TYPE: PRT
<213> ORGANISM: Artificial Sequence
<220> FEATURE:
<223> OTHER INFORMATION: 12-M11-A HC CDR2

<400> SEQUENCE: 95

Ile Asn Pro Ile Thr Gly Tyr Thr
1               5

<210> SEQ ID NO 96
```

```
<211> LENGTH: 15
<212> TYPE: PRT
<213> ORGANISM: Artificial Sequence
<220> FEATURE:
<223> OTHER INFORMATION: 12-M11-A HC CDR3

<400> SEQUENCE: 96

Ala Arg Gly Val Glu Asn Phe Asp Tyr Leu Tyr Ala Met Asp Tyr
1               5                   10                  15

<210> SEQ ID NO 97
<211> LENGTH: 8
<212> TYPE: PRT
<213> ORGANISM: Artificial Sequence
<220> FEATURE:
<223> OTHER INFORMATION: 5-C11-A HC CDR1

<400> SEQUENCE: 97

Gly Phe Thr Phe Ser Asp Phe Tyr
1               5

<210> SEQ ID NO 98
<211> LENGTH: 8
<212> TYPE: PRT
<213> ORGANISM: Artificial Sequence
<220> FEATURE:
<223> OTHER INFORMATION: 5-C11-A HC CDR2

<400> SEQUENCE: 98

Ile Ser Asp Gly Gly Ser Tyr Thr
1               5

<210> SEQ ID NO 99
<211> LENGTH: 14
<212> TYPE: PRT
<213> ORGANISM: Artificial Sequence
<220> FEATURE:
<223> OTHER INFORMATION: 5-C11-A HC CDR3

<400> SEQUENCE: 99

Ala Ser Gly Tyr Tyr Tyr Gly Ser Asp Tyr Val Met Asp Tyr
1               5                   10

<210> SEQ ID NO 100
<211> LENGTH: 8
<212> TYPE: PRT
<213> ORGANISM: Artificial Sequence
<220> FEATURE:
<223> OTHER INFORMATION: 16-J5-A HC CDR1

<400> SEQUENCE: 100

Gly Phe Thr Phe Ser Ser Phe Gly
1               5

<210> SEQ ID NO 101
<211> LENGTH: 8
<212> TYPE: PRT
<213> ORGANISM: Artificial Sequence
<220> FEATURE:
<223> OTHER INFORMATION: 16-J5-A HC CDR2

<400> SEQUENCE: 101

Ile Ser Ser Gly Ser Ser Thr Ile
1               5

<210> SEQ ID NO 102
<211> LENGTH: 11
```

```
<212> TYPE: PRT
<213> ORGANISM: Artificial Sequence
<220> FEATURE:
<223> OTHER INFORMATION: 16-J5-A HC CDR3

<400> SEQUENCE: 102

Ala Arg Trp Gly Arg Trp Ala Asp Phe Asp Tyr
1               5                   10

<210> SEQ ID NO 103
<211> LENGTH: 8
<212> TYPE: PRT
<213> ORGANISM: Artificial Sequence
<220> FEATURE:
<223> OTHER INFORMATION: 7-N2-A HC CDR1

<400> SEQUENCE: 103

Gly Phe Ser Leu Thr Gly Phe Gly
1               5

<210> SEQ ID NO 104
<211> LENGTH: 7
<212> TYPE: PRT
<213> ORGANISM: Artificial Sequence
<220> FEATURE:
<223> OTHER INFORMATION: 7-N2-A HC CDR2

<400> SEQUENCE: 104

Ile Trp Gly Asp Gly Ser Thr
1               5

<210> SEQ ID NO 105
<211> LENGTH: 14
<212> TYPE: PRT
<213> ORGANISM: Artificial Sequence
<220> FEATURE:
<223> OTHER INFORMATION: 7-N2-A HC CDR3

<400> SEQUENCE: 105

Ala Arg Asp Tyr Tyr Gly Tyr Val Gly Asn Ala Met Asp Tyr
1               5                   10

<210> SEQ ID NO 106
<211> LENGTH: 11
<212> TYPE: PRT
<213> ORGANISM: Artificial Sequence
<220> FEATURE:
<223> OTHER INFORMATION: 20-L10-A LC CDR1

<400> SEQUENCE: 106

Gln Ser Leu Val His Ser Asn Gly Asn Thr Tyr
1               5                   10

<210> SEQ ID NO 107
<211> LENGTH: 3
<212> TYPE: PRT
<213> ORGANISM: Artificial Sequence
<220> FEATURE:
<223> OTHER INFORMATION: 20-L10-A LC CDR2

<400> SEQUENCE: 107

Lys Val Ser
1

<210> SEQ ID NO 108
<211> LENGTH: 9
<212> TYPE: PRT
```

```
<213> ORGANISM: Artificial Sequence
<220> FEATURE:
<223> OTHER INFORMATION: 20-L10-A LC CDR3

<400> SEQUENCE: 108

Ser Gln Asn Thr His Val Pro Trp Thr
1               5

<210> SEQ ID NO 109
<211> LENGTH: 11
<212> TYPE: PRT
<213> ORGANISM: Artificial Sequence
<220> FEATURE:
<223> OTHER INFORMATION: 15-L23-A LC CDR1

<400> SEQUENCE: 109

Gln Ser Leu Val His Ser Asn Gly Asn Thr Tyr
1               5                   10

<210> SEQ ID NO 110
<211> LENGTH: 3
<212> TYPE: PRT
<213> ORGANISM: Artificial Sequence
<220> FEATURE:
<223> OTHER INFORMATION: 15-L23-A LC CDR2

<400> SEQUENCE: 110

Lys Val Ser
1

<210> SEQ ID NO 111
<211> LENGTH: 9
<212> TYPE: PRT
<213> ORGANISM: Artificial Sequence
<220> FEATURE:
<223> OTHER INFORMATION: 15-L23-A LC CDR3

<400> SEQUENCE: 111

Ser Gln Asn Thr His Val Pro Trp Thr
1               5

<210> SEQ ID NO 112
<211> LENGTH: 11
<212> TYPE: PRT
<213> ORGANISM: Artificial Sequence
<220> FEATURE:
<223> OTHER INFORMATION: 8-F3-A LC CDR1

<400> SEQUENCE: 112

Gln Ser Leu Val His Ser Asn Gly Asn Thr Tyr
1               5                   10

<210> SEQ ID NO 113
<211> LENGTH: 3
<212> TYPE: PRT
<213> ORGANISM: Artificial Sequence
<220> FEATURE:
<223> OTHER INFORMATION: 8-F3-A LC CDR2

<400> SEQUENCE: 113

Lys Val Ser
1

<210> SEQ ID NO 114
<211> LENGTH: 9
<212> TYPE: PRT
<213> ORGANISM: Artificial Sequence
```

```
<220> FEATURE:
<223> OTHER INFORMATION: 8-F3-A LC CDR3

<400> SEQUENCE: 114

Ser Gln Thr Thr His Val Pro Trp Thr
1               5

<210> SEQ ID NO 115
<211> LENGTH: 11
<212> TYPE: PRT
<213> ORGANISM: Artificial Sequence
<220> FEATURE:
<223> OTHER INFORMATION: 7-P15-A LC CDR1

<400> SEQUENCE: 115

Gln Ser Leu Val His Ser Asn Gly Asn Thr Tyr
1               5                   10

<210> SEQ ID NO 116
<211> LENGTH: 3
<212> TYPE: PRT
<213> ORGANISM: Artificial Sequence
<220> FEATURE:
<223> OTHER INFORMATION: 7-P15-A LC CDR2

<400> SEQUENCE: 116

Lys Val Ser
1

<210> SEQ ID NO 117
<211> LENGTH: 9
<212> TYPE: PRT
<213> ORGANISM: Artificial Sequence
<220> FEATURE:
<223> OTHER INFORMATION: 7-P15-A LC CDR3

<400> SEQUENCE: 117

Ser Gln Ser Ile His Val Pro Tyr Thr
1               5

<210> SEQ ID NO 118
<211> LENGTH: 12
<212> TYPE: PRT
<213> ORGANISM: Artificial Sequence
<220> FEATURE:
<223> OTHER INFORMATION: 18-N1-A LC CDR1

<400> SEQUENCE: 118

Gln Ser Leu Leu Asn Ser Arg Thr Arg Lys Asn Tyr
1               5                   10

<210> SEQ ID NO 119
<211> LENGTH: 3
<212> TYPE: PRT
<213> ORGANISM: Artificial Sequence
<220> FEATURE:
<223> OTHER INFORMATION: 18-N1-A LC CDR2

<400> SEQUENCE: 119

Trp Ala Ser
1

<210> SEQ ID NO 120
<211> LENGTH: 8
<212> TYPE: PRT
<213> ORGANISM: Artificial Sequence
<220> FEATURE:
```

<223> OTHER INFORMATION: 18-N1-A LC CDR3

<400> SEQUENCE: 120

Lys Gln Ser Tyr Asn Leu Tyr Thr
1               5

<210> SEQ ID NO 121
<211> LENGTH: 10
<212> TYPE: PRT
<213> ORGANISM: Artificial Sequence
<220> FEATURE:
<223> OTHER INFORMATION: 18-O22-A LC CDR1

<400> SEQUENCE: 121

Gln Ser Val Asp Tyr Asp Gly Glu Ser Tyr
1               5                   10

<210> SEQ ID NO 122
<211> LENGTH: 3
<212> TYPE: PRT
<213> ORGANISM: Artificial Sequence
<220> FEATURE:
<223> OTHER INFORMATION: 18-O22-A LC CDR2

<400> SEQUENCE: 122

Val Ala Ser
1

<210> SEQ ID NO 123
<211> LENGTH: 10
<212> TYPE: PRT
<213> ORGANISM: Artificial Sequence
<220> FEATURE:
<223> OTHER INFORMATION: 18-O22-A LC CDR3

<400> SEQUENCE: 123

Gln Gln Ser Asn Glu Asp Pro Thr Trp Thr
1               5                   10

<210> SEQ ID NO 124
<211> LENGTH: 7
<212> TYPE: PRT
<213> ORGANISM: Artificial Sequence
<220> FEATURE:
<223> OTHER INFORMATION: 16-L3-A LC CDR1

<400> SEQUENCE: 124

Ser Ser Ile Ser Ser Ser Asn
1               5

<210> SEQ ID NO 125
<211> LENGTH: 3
<212> TYPE: PRT
<213> ORGANISM: Artificial Sequence
<220> FEATURE:
<223> OTHER INFORMATION: 16-L3-A LC CDR2

<400> SEQUENCE: 125

Gly Thr Ser
1

<210> SEQ ID NO 126
<211> LENGTH: 9
<212> TYPE: PRT
<213> ORGANISM: Artificial Sequence
<220> FEATURE:
<223> OTHER INFORMATION: 16-L3-A LC CDR3

<400> SEQUENCE: 126

Gln Gln Trp Ser Ser Tyr Pro Leu Thr
1               5

<210> SEQ ID NO 127
<211> LENGTH: 6
<212> TYPE: PRT
<213> ORGANISM: Artificial Sequence
<220> FEATURE:
<223> OTHER INFORMATION: 16-K5-A LC CDR1

<400> SEQUENCE: 127

Gln Asp Ile Asn Ser Tyr
1               5

<210> SEQ ID NO 128
<211> LENGTH: 3
<212> TYPE: PRT
<213> ORGANISM: Artificial Sequence
<220> FEATURE:
<223> OTHER INFORMATION: 16-K5-A LC CDR2

<400> SEQUENCE: 128

Arg Ala Asp
1

<210> SEQ ID NO 129
<211> LENGTH: 9
<212> TYPE: PRT
<213> ORGANISM: Artificial Sequence
<220> FEATURE:
<223> OTHER INFORMATION: 16-K5-A LC CDR3

<400> SEQUENCE: 129

Leu Gln Tyr Asp Glu Phe Pro Leu Thr
1               5

<210> SEQ ID NO 130
<211> LENGTH: 10
<212> TYPE: PRT
<213> ORGANISM: Artificial Sequence
<220> FEATURE:
<223> OTHER INFORMATION: 19-A14-A LC CDR1

<400> SEQUENCE: 130

Glu Ser Val Asp Asn Tyr Gly Ile Ser Phe
1               5                   10

<210> SEQ ID NO 131
<211> LENGTH: 3
<212> TYPE: PRT
<213> ORGANISM: Artificial Sequence
<220> FEATURE:
<223> OTHER INFORMATION: 19-A14-A LC CDR2

<400> SEQUENCE: 131

Ala Ala Ser
1

<210> SEQ ID NO 132
<211> LENGTH: 9
<212> TYPE: PRT
<213> ORGANISM: Artificial Sequence
<220> FEATURE:
<223> OTHER INFORMATION: 19-A14-A LC CDR3

```
<400> SEQUENCE: 132

His Gln Ser Lys Glu Val Pro Trp Thr
1               5

<210> SEQ ID NO 133
<211> LENGTH: 6
<212> TYPE: PRT
<213> ORGANISM: Artificial Sequence
<220> FEATURE:
<223> OTHER INFORMATION: 2-K2-A LC CDR1

<400> SEQUENCE: 133

Gln Gly Ile Ser Ser Asn
1               5

<210> SEQ ID NO 134
<211> LENGTH: 3
<212> TYPE: PRT
<213> ORGANISM: Artificial Sequence
<220> FEATURE:
<223> OTHER INFORMATION: 2-K2-A LC CDR2

<400> SEQUENCE: 134

His Gly Thr
1

<210> SEQ ID NO 135
<211> LENGTH: 9
<212> TYPE: PRT
<213> ORGANISM: Artificial Sequence
<220> FEATURE:
<223> OTHER INFORMATION: 2-K2-A LC CDR3

<400> SEQUENCE: 135

Val Gln Tyr Ala Gln Phe Pro Phe Thr
1               5

<210> SEQ ID NO 136
<211> LENGTH: 10
<212> TYPE: PRT
<213> ORGANISM: Artificial Sequence
<220> FEATURE:
<223> OTHER INFORMATION: 6-H6-A LC CDR1

<400> SEQUENCE: 136

Gln Ser Val Ser Thr Ser Ser Tyr Ser Phe
1               5                   10

<210> SEQ ID NO 137
<211> LENGTH: 3
<212> TYPE: PRT
<213> ORGANISM: Artificial Sequence
<220> FEATURE:
<223> OTHER INFORMATION: 6-H6-A LC CDR2

<400> SEQUENCE: 137

Tyr Ala Ser
1

<210> SEQ ID NO 138
<211> LENGTH: 9
<212> TYPE: PRT
<213> ORGANISM: Artificial Sequence
<220> FEATURE:
<223> OTHER INFORMATION: 6-H6-A LC CDR3

<400> SEQUENCE: 138
```

```
Gln His Ser Trp Glu Ile Pro Pro Thr
1               5

<210> SEQ ID NO 139
<211> LENGTH: 10
<212> TYPE: PRT
<213> ORGANISM: Artificial Sequence
<220> FEATURE:
<223> OTHER INFORMATION: 1-A19-A LC CDR1

<400> SEQUENCE: 139

Gln Ser Val Asp Tyr Asp Gly Asp Ser Tyr
1               5                   10

<210> SEQ ID NO 140
<211> LENGTH: 3
<212> TYPE: PRT
<213> ORGANISM: Artificial Sequence
<220> FEATURE:
<223> OTHER INFORMATION: 1-A19-A LC CDR2

<400> SEQUENCE: 140

Ala Ala Ser
1

<210> SEQ ID NO 141
<211> LENGTH: 9
<212> TYPE: PRT
<213> ORGANISM: Artificial Sequence
<220> FEATURE:
<223> OTHER INFORMATION: 1-A19-A LC CDR3

<400> SEQUENCE: 141

Gln Gln Ser Asn Glu Asp Pro Phe Thr
1               5

<210> SEQ ID NO 142
<211> LENGTH: 10
<212> TYPE: PRT
<213> ORGANISM: Artificial Sequence
<220> FEATURE:
<223> OTHER INFORMATION: 10-O15-A LC CDR1

<400> SEQUENCE: 142

Lys Ser Val Ser Ala Ser Gly Tyr Ser Tyr
1               5                   10

<210> SEQ ID NO 143
<211> LENGTH: 3
<212> TYPE: PRT
<213> ORGANISM: Artificial Sequence
<220> FEATURE:
<223> OTHER INFORMATION: 10-O15-A LC CDR2

<400> SEQUENCE: 143

Leu Ala Ser
1

<210> SEQ ID NO 144
<211> LENGTH: 9
<212> TYPE: PRT
<213> ORGANISM: Artificial Sequence
<220> FEATURE:
<223> OTHER INFORMATION: 10-O15-A LC CDR3

<400> SEQUENCE: 144
```

```
Gln His Ser Arg Glu Leu Pro Phe Thr
1               5

<210> SEQ ID NO 145
<211> LENGTH: 10
<212> TYPE: PRT
<213> ORGANISM: Artificial Sequence
<220> FEATURE:
<223> OTHER INFORMATION: 6-I13-A LC CDR1

<400> SEQUENCE: 145

Lys Ser Val Ser Thr Ser Gly Tyr Ser Tyr
1               5                   10

<210> SEQ ID NO 146
<211> LENGTH: 3
<212> TYPE: PRT
<213> ORGANISM: Artificial Sequence
<220> FEATURE:
<223> OTHER INFORMATION: 6-I13-A LC CDR2

<400> SEQUENCE: 146

Leu Ala Ser
1

<210> SEQ ID NO 147
<211> LENGTH: 9
<212> TYPE: PRT
<213> ORGANISM: Artificial Sequence
<220> FEATURE:
<223> OTHER INFORMATION: 6-I13-A LC CDR3

<400> SEQUENCE: 147

Gln His Ser Arg Glu Leu Pro Tyr Thr
1               5

<210> SEQ ID NO 148
<211> LENGTH: 10
<212> TYPE: PRT
<213> ORGANISM: Artificial Sequence
<220> FEATURE:
<223> OTHER INFORMATION: 5-K4-A LC CDR1

<400> SEQUENCE: 148

Glu Ser Val Glu Tyr Tyr Gly Thr Ser Leu
1               5                   10

<210> SEQ ID NO 149
<211> LENGTH: 3
<212> TYPE: PRT
<213> ORGANISM: Artificial Sequence
<220> FEATURE:
<223> OTHER INFORMATION: 5-K4-A LC CDR2

<400> SEQUENCE: 149

Ala Ala Ser
1

<210> SEQ ID NO 150
<211> LENGTH: 9
<212> TYPE: PRT
<213> ORGANISM: Artificial Sequence
<220> FEATURE:
<223> OTHER INFORMATION: 5-K4-A LC CDR3

<400> SEQUENCE: 150

Gln Gln Ser Arg Lys Val Pro Trp Thr
```

```
<210> SEQ ID NO 151
<211> LENGTH: 10
<212> TYPE: PRT
<213> ORGANISM: Artificial Sequence
<220> FEATURE:
<223> OTHER INFORMATION: 12-G18-A LC CDR1

<400> SEQUENCE: 151

Glu Ser Val Asp Asn Tyr Gly Ile Ser Phe
1               5                   10

<210> SEQ ID NO 152
<211> LENGTH: 3
<212> TYPE: PRT
<213> ORGANISM: Artificial Sequence
<220> FEATURE:
<223> OTHER INFORMATION: 12-G18-A LC CDR2

<400> SEQUENCE: 152

Ala Glu Ser
1

<210> SEQ ID NO 153
<211> LENGTH: 9
<212> TYPE: PRT
<213> ORGANISM: Artificial Sequence
<220> FEATURE:
<223> OTHER INFORMATION: 12-G18-A LC CDR3

<400> SEQUENCE: 153

Gln Gln Ser Lys Glu Val Pro Tyr Thr
1               5

<210> SEQ ID NO 154
<211> LENGTH: 6
<212> TYPE: PRT
<213> ORGANISM: Artificial Sequence
<220> FEATURE:
<223> OTHER INFORMATION: 10-M21-A LC CDR1

<400> SEQUENCE: 154

Gln Asp Ile Asn Arg Tyr
1               5

<210> SEQ ID NO 155
<211> LENGTH: 3
<212> TYPE: PRT
<213> ORGANISM: Artificial Sequence
<220> FEATURE:
<223> OTHER INFORMATION: 10-M21-A LC CDR2

<400> SEQUENCE: 155

Tyr Thr Ser
1

<210> SEQ ID NO 156
<211> LENGTH: 9
<212> TYPE: PRT
<213> ORGANISM: Artificial Sequence
<220> FEATURE:
<223> OTHER INFORMATION: 10-M21-A LC CDR3

<400> SEQUENCE: 156

Leu Gln Tyr Asp Asn Leu Leu Phe Thr
1               5
```

```
<210> SEQ ID NO 157
<211> LENGTH: 5
<212> TYPE: PRT
<213> ORGANISM: Artificial Sequence
<220> FEATURE:
<223> OTHER INFORMATION: 12-M11-A LC CDR1

<400> SEQUENCE: 157

Ser Ser Ile Ser Tyr
1               5

<210> SEQ ID NO 158
<211> LENGTH: 3
<212> TYPE: PRT
<213> ORGANISM: Artificial Sequence
<220> FEATURE:
<223> OTHER INFORMATION: 12-M11-A LC CDR2

<400> SEQUENCE: 158

Asp Thr Ser
1

<210> SEQ ID NO 159
<211> LENGTH: 8
<212> TYPE: PRT
<213> ORGANISM: Artificial Sequence
<220> FEATURE:
<223> OTHER INFORMATION: 12-M11-A LC CDR3

<400> SEQUENCE: 159

His Gln Arg Ser Ser Tyr Arg Thr
1               5

<210> SEQ ID NO 160
<211> LENGTH: 12
<212> TYPE: PRT
<213> ORGANISM: Artificial Sequence
<220> FEATURE:
<223> OTHER INFORMATION: 5-C11-A LC CDR1

<400> SEQUENCE: 160

Gln Ser Leu Leu Asn Ser Arg Thr Arg Lys Asn Tyr
1               5                   10

<210> SEQ ID NO 161
<211> LENGTH: 3
<212> TYPE: PRT
<213> ORGANISM: Artificial Sequence
<220> FEATURE:
<223> OTHER INFORMATION: 5-C11-A LC CDR2

<400> SEQUENCE: 161

Trp Ala Ser
1

<210> SEQ ID NO 162
<211> LENGTH: 8
<212> TYPE: PRT
<213> ORGANISM: Artificial Sequence
<220> FEATURE:
<223> OTHER INFORMATION: 5-C11-A LC CDR3

<400> SEQUENCE: 162

Lys Gln Ser Tyr Asn Leu Leu Thr
1               5
```

<210> SEQ ID NO 163
<211> LENGTH: 10
<212> TYPE: PRT
<213> ORGANISM: Artificial Sequence
<220> FEATURE:
<223> OTHER INFORMATION: 16-J5-A LC CDR1

<400> SEQUENCE: 163

Gln Ser Val Asp Tyr Asp Gly Asp Ser Tyr
1               5                   10

<210> SEQ ID NO 164
<211> LENGTH: 3
<212> TYPE: PRT
<213> ORGANISM: Artificial Sequence
<220> FEATURE:
<223> OTHER INFORMATION: 16-J5-A LC CDR2

<400> SEQUENCE: 164

Ala Ala Ser
1

<210> SEQ ID NO 165
<211> LENGTH: 9
<212> TYPE: PRT
<213> ORGANISM: Artificial Sequence
<220> FEATURE:
<223> OTHER INFORMATION: 16-J5-A LC CDR3

<400> SEQUENCE: 165

Gln Gln Ser Asn Glu Asp Pro Pro Thr
1               5

<210> SEQ ID NO 166
<211> LENGTH: 12
<212> TYPE: PRT
<213> ORGANISM: Artificial Sequence
<220> FEATURE:
<223> OTHER INFORMATION: 7-N2-A LC CDR1

<400> SEQUENCE: 166

Gln Ser Leu Leu Asn Ser Arg Thr Arg Lys Asn Tyr
1               5                   10

<210> SEQ ID NO 167
<211> LENGTH: 3
<212> TYPE: PRT
<213> ORGANISM: Artificial Sequence
<220> FEATURE:
<223> OTHER INFORMATION: 7-N2-A LC CDR2

<400> SEQUENCE: 167

Trp Ala Ser
1

<210> SEQ ID NO 168
<211> LENGTH: 9
<212> TYPE: PRT
<213> ORGANISM: Artificial Sequence
<220> FEATURE:
<223> OTHER INFORMATION: 7-N2-A LC CDR3

<400> SEQUENCE: 168

Lys Gln Ser Tyr Asn His Met Tyr Thr
1               5

```
<210> SEQ ID NO 169
<211> LENGTH: 7
<212> TYPE: PRT
<213> ORGANISM: Artificial Sequence
<220> FEATURE:
<223> OTHER INFORMATION: HC CDR3
<220> FEATURE:
<221> NAME/KEY: Xaa
<222> LOCATION: (4)..(4)
<223> OTHER INFORMATION: Xaa is Ala, Thr, or Leu
<220> FEATURE:
<221> NAME/KEY: Xaa
<222> LOCATION: (5)..(5)
<223> OTHER INFORMATION: Xaa is Met or Glu

<400> SEQUENCE: 169

Ala Arg Asp Xaa Xaa Asp Tyr
1               5

<210> SEQ ID NO 170
<211> LENGTH: 9
<212> TYPE: PRT
<213> ORGANISM: Artificial Sequence
<220> FEATURE:
<223> OTHER INFORMATION: LC CDR3
<220> FEATURE:
<221> NAME/KEY: Xaa
<222> LOCATION: (3)..(3)
<223> OTHER INFORMATION: Xaa is Asn, Thr, or Ser
<220> FEATURE:
<221> NAME/KEY: Xaa
<222> LOCATION: (4)..(4)
<223> OTHER INFORMATION: Xaa is Thr or Ile
<220> FEATURE:
<221> NAME/KEY: Xaa
<222> LOCATION: (8)..(8)
<223> OTHER INFORMATION: Xaa is Trp or Tyr

<400> SEQUENCE: 170

Ser Gln Xaa Xaa His Val Pro Xaa Thr
1               5

<210> SEQ ID NO 171
<211> LENGTH: 113
<212> TYPE: PRT
<213> ORGANISM: Artificial Sequence
<220> FEATURE:
<223> OTHER INFORMATION: H1 Heavy Chain Variable Region

<400> SEQUENCE: 171

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Ser
            20                  25                  30

Asp Ile Asn Trp Val Arg Gln Ala Pro Gly Lys Gly Leu Val Trp Ile
        35                  40                  45

Gly Trp Ile Phe Pro Gly Asp Gly Ser Thr Lys Tyr Thr Pro Ser Leu
    50                  55                  60

Lys Asp Gln Ala Thr Leu Ser Thr Asp Lys Lys Asn Thr Ala Tyr
65                  70                  75                  80

Leu Gln Met Asn Ser Leu Arg Ala Glu Asp Thr Ala Val Tyr Phe Cys
                85                  90                  95

Ala Arg Gly Leu Asp Tyr Trp Gly Gln Gly Thr Leu Val Thr Val Ser
            100                 105                 110

Ser
```

```
<210> SEQ ID NO 172
<211> LENGTH: 113
<212> TYPE: PRT
<213> ORGANISM: Artificial Sequence
<220> FEATURE:
<223> OTHER INFORMATION: H2 Heavy Chain Variable Region

<400> SEQUENCE: 172
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Ser
            20                  25                  30

Asp Ile Asn Trp Val Arg Gln Ala Pro Gly Lys Gly Leu Val Trp Ile
        35                  40                  45

Gly Trp Ile Phe Pro Gly Asp Gly Ser Thr Lys Tyr Thr Pro Ser Leu
    50                  55                  60

Lys Asp Gln Ala Thr Leu Ser Thr Asp Leu Ala Lys Asn Thr Ala Tyr
65                  70                  75                  80

Leu Gln Met Asn Ser Leu Arg Ala Glu Asp Thr Ala Val Tyr Phe Cys
                85                  90                  95

Ala Arg Gly Leu Asp Tyr Trp Gly Gln Gly Thr Leu Val Thr Val Ser
            100                 105                 110

Ser

```
<210> SEQ ID NO 173
<211> LENGTH: 113
<212> TYPE: PRT
<213> ORGANISM: Artificial Sequence
<220> FEATURE:
<223> OTHER INFORMATION: H5 Heavy Chain Variable Region

<400> SEQUENCE: 173
```

Gln Val Gln Leu Gln Glu Ser Gly Pro Gly Leu Val Lys Pro Ser Glu
1               5                   10                  15

Thr Leu Ser Leu Thr Cys Thr Ala Ser Gly Tyr Thr Phe Thr Ser Ser
            20                  25                  30

Asp Ile Asn Trp Val Arg Gln Pro Pro Gly Lys Gly Leu Glu Trp Ile
        35                  40                  45

Gly Trp Ile Phe Pro Gly Asp Gly Ser Thr Lys Tyr Asn Pro Ser Leu
    50                  55                  60

Lys Ser Arg Ala Thr Leu Ser Thr Asp Lys Ser Lys Asn Gln Ala Ser
65                  70                  75                  80

Leu Asn Leu Asp Ser Val Ser Ala Ala Asp Thr Ala Ile Tyr Phe Cys
                85                  90                  95

Ala Arg Gly Leu Asp Tyr Trp Gly Lys Gly Thr Val Thr Val Ser
            100                 105                 110

Ser

```
<210> SEQ ID NO 174
<211> LENGTH: 113
<212> TYPE: PRT
<213> ORGANISM: Artificial Sequence
<220> FEATURE:
<223> OTHER INFORMATION: H7 Heavy Chain Variable Region

<400> SEQUENCE: 174
```

Gln Val Gln Leu Gln Glu Ser Gly Pro Gly Leu Val Lys Pro Ser Glu
1               5                   10                  15

Thr Leu Ser Leu Thr Cys Lys Ala Ser Gly Tyr Thr Phe Thr Ser Ser

```
                    20                  25                  30
Asp Ile Asn Trp Val Arg Gln Pro Pro Gly Lys Gly Leu Glu Trp Ile
                35                  40                  45

Gly Trp Ile Phe Pro Gly Asp Gly Ser Thr Lys Tyr Asn Pro Ser Leu
 50                  55                  60

Lys Ser Arg Ala Thr Leu Ser Thr Asp Lys Ser Lys Asn Gln Ala Ser
 65                  70                  75                  80

Leu Asn Leu Ser Ser Val Thr Ala Ala Asp Thr Ala Val Tyr Phe Cys
                 85                  90                  95

Ala Arg Gly Leu Asp Tyr Trp Gly Lys Gly Thr Thr Val Thr Val Ser
                100                 105                 110

Ser

<210> SEQ ID NO 175
<211> LENGTH: 107
<212> TYPE: PRT
<213> ORGANISM: Artificial Sequence
<220> FEATURE:
<223> OTHER INFORMATION: L1 Light Chain Variable Region

<400> SEQUENCE: 175

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Ser Tyr
                20                  25                  30

Leu Gly Trp Phe Gln Gln Lys Pro Gly Lys Ala Pro Lys Thr Leu Ile
                35                  40                  45

Tyr Arg Ala Asp Arg Leu Val Asp Gly Val Pro Ser Arg Phe Ser Gly
 50                  55                  60

Ser Gly Ser Gly Gln Asp Tyr Thr Phe Thr Ile Ser Ser Leu Gln Pro
 65                  70                  75                  80

Glu Asp Ile Ala Thr Tyr Tyr Cys Leu Gln Tyr Asp Glu Phe Pro Leu
                 85                  90                  95

Thr Phe Gly Gln Gly Thr Lys Leu Glu Ile Lys
                100                 105

<210> SEQ ID NO 176
<211> LENGTH: 107
<212> TYPE: PRT
<213> ORGANISM: Artificial Sequence
<220> FEATURE:
<223> OTHER INFORMATION: L5 Light Chain Variable Region

<400> SEQUENCE: 176

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Ser Tyr
                20                  25                  30

Leu Gly Trp Phe Gln Gln Lys Pro Gly Lys Ala Pro Lys Thr Leu Ile
                35                  40                  45

Tyr Arg Ala Asp Arg Leu Val Asp Gly Val Pro Ser Arg Phe Ser Gly
 50                  55                  60

Ser Gly Ser Gly Gln Asp Tyr Thr Phe Thr Ile Ser Ser Leu Gln Pro
 65                  70                  75                  80

Glu Asp Ile Ala Thr Tyr Tyr Cys Leu Gln Tyr Asp Glu Phe Pro Leu
                 85                  90                  95

Thr Phe Gly Pro Gly Thr Lys Val Asp Ile Lys
```

```
                  100             105

<210> SEQ ID NO 177
<211> LENGTH: 301
<212> TYPE: PRT
<213> ORGANISM: Homo sapiens

<400> SEQUENCE: 177

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
            195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
    290                 295                 300
```